US006420545B1

(12) United States Patent
Hoxie et al.

(10) Patent No.: US 6,420,545 B1
(45) Date of Patent: Jul. 16, 2002

(54) CD4-INDEPENDENT HIV ENVELOPE PROTEINS AS VACCINES AND THERAPEUTICS

(75) Inventors: James A. Hoxie, Berwyn, PA (US); Celia C. LaBranche, Chapel Hill, NC (US); Robert W. Doms, Berwyn; Trevor L. Hoffman, Lansdowne, both of PA (US)

(73) Assignees: The Trustees of the University of Pennsylvania, Philadelphia, PA (US); Duke University, Durham, NC (US)

( * ) Notice: Subject to any disclaimer, the term of this patent is extended or adjusted under 35 U.S.C. 154(b) by 0 days.

(21) Appl. No.: 09/337,387

(22) Filed: Jun. 22, 1999

Related U.S. Application Data

(63) Continuation-in-part of application No. 09/317,556, filed on May 24, 1999.

(51) Int. Cl.[7] ................................................ C07H 21/04
(52) U.S. Cl. ............................... 536/23.72; 424/208.1; 435/69.1; 435/235.1; 435/320.1; 514/44; 536/23.1; 536/23.4; 935/32
(58) Field of Search ............................. 435/69.1, 235.1, 435/320.1; 536/23.1, 23.4, 23.72; 935/32; 514/44; 424/208.1

(56) References Cited

U.S. PATENT DOCUMENTS

| | | | |
|---|---|---|---|
| 4,160,452 A | | 7/1979 | Theeuwes |
| 4,256,108 A | | 3/1981 | Theeuwes |
| 4,265,874 A | | 5/1981 | Bonsen et al. |
| 5,871,732 A | * | 2/1999 | Burkly et al. ............ 424/133.1 |
| 6,001,997 A | * | 12/1999 | Chang et al. ............ 530/389.4 |

FOREIGN PATENT DOCUMENTS

EP            0552850 A1  *  7/1993

OTHER PUBLICATIONS

Hiraka et al. Differentiation of human embryonal carcinoma cells induce humna immunodeficiency virus permissivness which is stimulated by human cytomegalovirus coinefection. Journal of Virology. vol. 65, No. 5 (1991) PP. 2732–2735.*
Ngo et al., 1994, The Protein Folding Problem and Tertiary Structure Prediction, pp. 492–495.*
Alexander et al., 1992, 1992, J. Virol. 66:2934–2942.
Alkhatib et al., 1996, Science 272:1955–1958.
Bandres et al., 1998, J. Virol. 72:2500–2504.
Berger, 1997, AIDS 11:S3–S16.
Bird et al., 1988, Science 242:423–426.
Burger et al., 1991, J. Gen. Virol. 72:359–367.
Burton and Motefiori, 1997, AIDS 11 (Supp. A):S87–S98.
Cao et al., 1993, J. Virol. 67:2747–2755.
Cao et al., 1997, J. Virol. 71:9808–9812.
Chackerian et al., 1997, J. Virol. 71:3932–3939.
Chan et al., 1997, Cell 89:263–273.
Chen et al., 1996, Virology 226:260–268.
Cho et al., 1998, J. Virol. 72:2509–2515.
Choe et al., 1996, Cell 85:1135–1148.
Cocchi et al., 1996, Nature Med. 2:1244–1247.
Connor et al., 1995, Virology 206:935–944.
Connor et al., 1997, J. Exp. Med. 185:621–628.
Cranage et al., 1986, EMBO J. 5:3057–3063.
Deng et al., 1996, Nature 381:661–666.
Deng et al., 1997, Nature 388:296–300.
Doranz et al., 1996, Cell 85:1149–1158.
Doranz et al., 1999, J. Virol., 73:2752–2761.
Doranz et al., 1997, J. Exp. med. 186:1395–1400.
Dragic et al., 1996, Nature 381:667–673.
Dubay et al., 1992, J. Virol. 66:6616–6625.
Dumonceaux et al., 1998, J. Virol. 72:512–519.
Earl et al., 1997, J. Virol. 71:2674–2684.
Edinger et al., 1997, Proc. Natl. Acad. Sci. USA 94:14742–14747.
Endres et al., 1996, Cell 87:745–756.
Endres et al., 1997, Science 278:1462–1464.
Farzan et al., 1997, J. Exp. Med. 186:405–411.
Feng et al., 1996, Science 272:872–876.
Gibbs et al., 1994, AIDS Res. Hum. Retroviruses. 10:343–350.
Haigwood et al., 1992, J. Med. Primatol. 21:82–90.
Hesselgesser et al., 1997, Curr. Biol. 7:112–121.
Hill et al., 1997, J. Virol. 71:6296–6304.
Hoffman et al., 1998, Proc. Natl. Acad. Sci. U.S.A. 95:11360–11365.
Hoffman and Doms, 1998, AIDS 12:S17–S26.
Huston et al., 1988, Proc. Natl. Acad. Sci. USA 85:5879–5883.
Hoxie et al., 1985, Science 229:1400–1402.
Hwang et al., 1991, Science 253:71–74.
Jones et al., 1998, J. Biol. Chem. 273:404–409.
Kay et al., 1997, Proc. Natl. Acad. Sci. U.S.A. 94:12744–12746.
Kielian, 1995, Advances in Virus Res. 45:113–151.
Kilby et al., 1998, Nature Med. 4:1302–1307.
Kozak et al., 1997, J. Virol. 71:873–882.
Kwong et al., 1998, Nature 393:648–659.
LaBranche et al., 1995, J. Virol. 69:5217–5227.
LaCasse et al., 1999, Science 283:357–362.
Lapham et al., 1996, Science 274:602–605.
Lee et al., 1999, J. Biol. Chem., 274:9617–9616.
Liao et al., 1997, J. Exp. Med. 185:2015–2023.
Martin et al., 1997, Science 278:1470–1473.
Matthews et al., 1994, Immunol. Rev. 140:93–104.
Misse et al., 1998, J. Virol. 72:7280–7288.

(List continued on next page.)

*Primary Examiner*—Jeffrey Stucker
*Assistant Examiner*—Ulrike Winker
(74) *Attorney, Agent, or Firm*—Morgan, Lewis & Bockius, LLP

(57) ABSTRACT

The invention relates to novel CD4-independent HIV Envelope proteins and uses therefor.

3 Claims, 15 Drawing Sheets

OTHER PUBLICATIONS

Figure 1A:
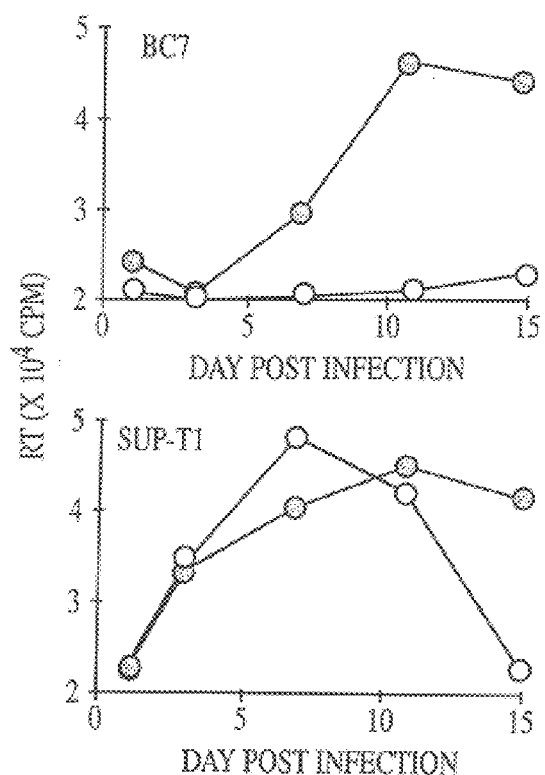
Figure 1B:
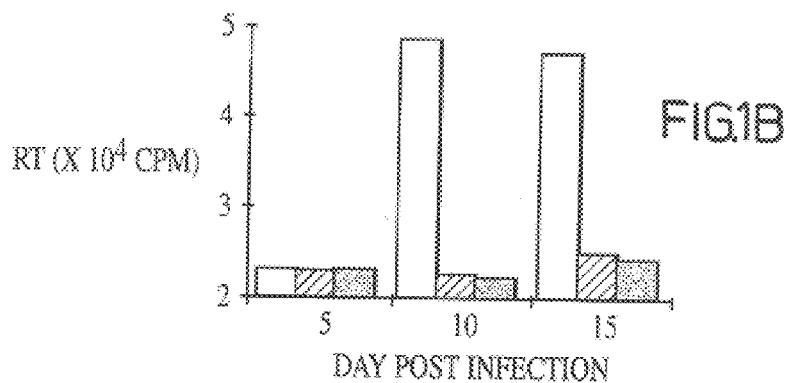
Figure 1C:
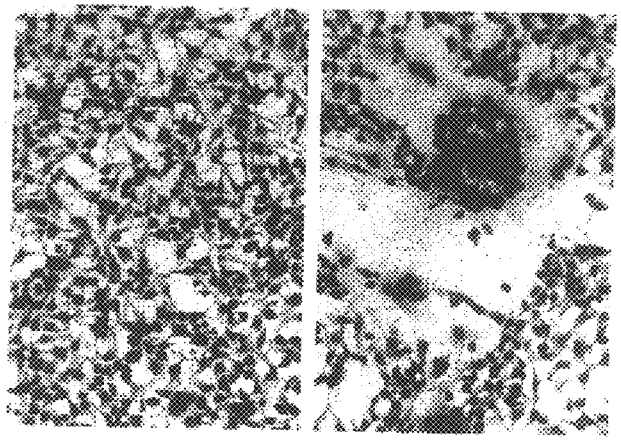

Moore and Ho, 1995, AIDS 9:S117–S136.
Moore et al., 1994, J. Virol. 68:469–484.
Mulligan et al., 1992, J. Virol. 66:3971–3975.
Olshevsky et al., 1990, J. Virol. 64:5701–5705.
Olson et al., 1999, J. Virol., in press.
Perelson et al., 1996, Science 271:1582–1586.
Platt et al., 1998, J. Virol. 72:2855–2864.
Pollard and Malim, 1998, Annu. Rev. Microbiol. 52:491–532.
Popovic et al., 1984, Science 225:497–500.
Reeves et al., 1996, J. Virol. 71:1453–1465.
Reeves and Schulz, 1996, J. Virol. 71:1453–1465.
Reitter et al., 1998, Nature Med. 4:679–684.
Ritter et al., 1993, Virology 197:255–264.
Rizzuto et al., 1998, Science 280:1949–1953.
Ross and Cullen, 1998, Proc. Natl. Acad. Sci. U.S.A. 95:7682–7686.
Ross et al., 1997, J. Virol. 72:1918–1924.
Ross et al., 1998, Proc. Natl. Acad. Sci. U.S.A. 95:7682–7686.
Rucker et al., 1997, Methods Enzymol. 288:118–133.
Rucker et al., 1997, J. Virol. 71:8999–9007.
Shimizu et al., 1992, Virology 189:534–546.
Speck et al., 1997, J. Virol. 71:7136–7139.
Spies et al., 1994, J. Virol. 68:585–591.
Stamamatos and Cheng–Mayer, 1998, J. Virol. 72:7840–7845.
Thali et al., 1993, J. Virol. 67:3978–3988.
Trkola et al., 1996, Nature 384:184–187.
Trkola et al., 1998, J. Virol. 72:1876–1885.
Wei et al., 1995, Nature 373:117–122.
Wu et al., 1996, Nature 384:179–183.
Wu et al., 1997, J. Exp. Med.
Wyatt et al., 1998, Nature 393:705–710.
Wyat et al., 1995, J. Virol. 69:5723–5733.
Wyatt et al., 1992, J. Virol. 66:6997–7004.
Wyatt and Sodroski, 1998, Science 280:1884–1888.
Zhang et al., 1998, J. Virol. 72:9337–9344.

* cited by examiner

```
ATGAGAGTGAAGGAGAGAAATATCAGCACTTGTGTGGAGATGGGGGTGGAGATGGGGCACCATGCTCCTTGGAGATGTTGA
TGATCTGTAATGCTACAGAAAAAATTGTGGGTCACAGTTCATTATGGGTACCTGTGTGGAAGGAAGCAACCACCAC
TCTATTTGTGCATCAGATGCTAAAGCATATGAAACAGAGGTACATAATGTTTGGCCACACATGCCTGTGTACCC
ACAGACCCCAACCCACAAGAAGTAGTATTGGTAAATGTGACAGAAAATTTAACATGTGGAAAAATGACATGGTAG
AACAGATGCATGAGGATATAATCAGTTTATGGGATCAAAGCCTAAAGCCATGTGTAAAATTAACCCCACTCTGTGT
TAGTTTAAAGTGCACTGATTGAAGAATGATACTAATACCAATAGTGGTAGCGGGAGAATGATAATGGAGAAAGGA
GAGATAAAAAACTGCTCTTTCAATATCAGCACAAGCAAAAGAAGTAAGGTGAAGAAAGAATATGCATTTTTTATA
AACTTGATATATAATACCAATAGATAATGATCCTACCAGCTATACGTTGACAAGTTGTAACACCTCAGTCATTACACA
GGCCTGTCCAAAGGTATCCTTTGAGCCAATTCCCATACATTATTGTGCCCCGGCTGGTTTTGCGATTCTAAAATGT
AATAATAAGACGTTCAATGGAACAGGACCATGTACAAATGTCAGCACAGTACAATGTACACATGGAATTAGGCCAG
TAGTATCAACTCAACTGCTGTTAAATGGCAGTCTGAACAGAAGAGAGTAGTAATTAGTGTCAATTCACGGA
CAATGCTAAAACCATATAAGTACAGCTGAACACATCTGTAGAAATTAATTGTACAAACCAACAACAATACAAGA
AAAAGAATCCGTATCCATAGAGGACCAGGGAGAGCATTTGTTACAGTGGAAAAATAGGAGAACAATTGGAAA
ATTGTAACATTAGTAGACAAAATGGAGTAACACTTTAAAACAGATAGCTAGCAAATTGTAACGCACAGTTTTAATTGTGGAGGG
TAATAAAACAATAATCTTTAAGCAGTCCTCAGGAGGGACCCAGAAATTGTAACTAAAGGTCAAATAACACTGAAGGAA
GAATTTTCTACTGTAAGTCAACACAACTGTTTAATAGTACTTGGAGTACTAAAGGTCAAATAACACTGAAGGAA
GTGACACAATCACCCTCCCATGCAGAATAAAACAAGTTATAAACATGTGGCAGGAAGTAGGAAAAGCAATGTATGC
CCCTCCCATCAGTGGACAAATTAGATGTTCATCAAATATTACAGGGCTGCTATTAACAAGAGATGGTGGTAATAGC
AACAATGAGTCCGAGATCTTCAGACCTGGAGGAGGAGATATGAGGGACAAATTGGAGAAGAACAATTGGAGAAGAATTATATAAATATA
AAGTAGTAAAAATTGAACCATTAGGAGTAGCACCCACCAAGGCAAAGAGAAGAGTGGTGCAGAGAGAAAAGAGC
AGTGGGAATAGGAGAGCTTTGTTCCTTGGTTCTCTTGGGAGCACTATGGGCGCAGCGTCAATGGCGCTG
ACGGTACAGCCAGACAATCATTGTCTGGTATAGTGCAGCAGCAGAACAATCTGCTGAGGGCTATTGAGGCGCAAC
AGCATCTGTTGCAACTCACAGTCTGGGCATCAAGCAGCTCCAGGCAAGAATCCTGGCTGTGGAAAGATACCTAAA
GGATCAACAGCTCCTGGGATTTGGGGTTGCTCTGGAAAACTCATTTGCACCACTGCTGTGCCTTGGAATGCTAGT
TGGAGTAATAAATCTCTGGAACAGATTTGGAATAACATGACCTGGATGGAGTGGGACAGAGAAATTAACAATTACA
```

FIG.14A

CAAGCTTAATACACTCCTTAATTGAAGAATCGCAAATCCAGCAAGAATGAACAAGAATTATTGGAATTAGA
TAAATGGGCAAGTTTGTGGAATTGGTTTAACATAACAAATTGGCTGTGGTATATAAAATTATTCATAATGATAGTA
GGAGGCTTGGTAGGTTTAAGAATAGTTTTTGCTGTGTACTTTCTGTAGTGAAAAAGTTAGGCAGGGATATTCACCATT
ATCGTTTCAGACCCACCTCCCAACACCGAGGGACCCGACAGGCCCGAAGGAATAG

FIG.14B

CD4-INDEPENDENT HIV ENVELOPE PROTEINS AS VACCINES AND THERAPEUTICS

CROSS REFERENCE TO RELATED APPLICATIONS

This application is a continuation-in-part of U.S. application Ser. No. 09/317,556 filed May 24, 1999.

STATEMENT REGARDING FEDERAL SPONSORSHIP

This invention was supported in part by funds from the U.S. Government (National Institutes of Health Grant No. AI44308 and Grant No. AI40880) and the U.S. Government may therefore have certain rights in the invention.

BACKGROUND OF THE INVENTION

The present invention relates to CD4-independent variants of HIV, their proteins, and uses therefor.

HIV entry is known to require an interaction of the viral envelope glycoprotein (Env) with CD4 and cellular chemokine receptors. HIV Env protein is produced as a precursor (gp160) that is subsequently cleaved into two parts, gp120 which binds CD4 and chemokine receptors, and gp41 which is anchored in the viral membrane and mediates membrane fusion. Differential use of chemokine receptors by HIV and SIV has largely explained differences in tropism among different isolates (Berger, 1997, AIDS 11:S3–S16; Hoffman and Doms, 1998, AIDS 12:S17–S26). While a number of chemokine receptors can be utilized by HIV or SIV (Deng et al., 1997, Nature 388:296–300; Choe et al., 1996, Cell 85, 1135–1148; Rucker et al., 1997, J. Virol. 71:8999–9007; Edinger et al., 1997, Proc. Natl. Acad. Sci. USA 94:14742–14747; Liao et al., 1997, J. Exp. Med. 185:2015–2023; Farzan et al., 1997, J. Exp. Med. 186:405–411), CCR5 and CXCR4 appear to be the principal coreceptors for HIV-1 (Zhang et al., 1998, J Virol. 72:9337–9344; Zhang et al., 1998, J. Virol. 72:9337–9344.). Isolates of HIV that first establish infection target blood lymphocytes and macrophages using CCR5 (Alkhatib et al., 1996, Science 272:1955–1958; Deng et al., 1996, Nature 381:661–666; Dragic et al., 1996, Nature 381:667–673; Doranz et al., 1996, Cell 85:1149–1158), while viruses that are generally associated with progression to AIDS and can infect T cell lines in vitro use CXCR4 (Choe et al., 1996, Cell 85:1135–1148; Feng et al., 1996, Science 272:872–876; Connor et al., 1997, J. Exp. Med. 185:621–628).

Binding of Env to CD4 initiates poorly understood conformational changes enabling gp120 to bind to a chemokine receptor and leading to fusion of the viral and cellular membranes (Jones et al., 1998, J. Biol Chem. 273:404409; Moore et al., 1994, J. Virol. 68:469–484; Wyatt, 1992, J. Virol. 66:6997–7004; Wu et al., 1996, Nature 384:179–183). Immunologic and mutagenesis approaches have indicated that these changes involve movement of V1/V2 and V3 hypervariable loops on gp120 (Moore, et al., 1994, J. Virol. 68:469–484; Wyatt et al., 1992, J. Virol. 66:6997–7004; Wu et al., 1996, Nature 384:179–183), which play a critical role in the specificity of chemokine receptor utilization (Choe et al., 1996, Cell 85:1135–1148; Cocchi et al., 1996, Nature Med 2:1244–1247; Cho et al., 1998, J. Virol. 72:2509–2515; Speck et al., 1997, J. Virol. 71:7136–7139; Ross et al., 1998, Proc. Natl. Acad. Sci. U.S.A. 95:7682–7686; Hoffman et al., 1998, Proc. Natl. Acad. Sci. U.S.A. 95:11360–11365). The recent crystallographic resolution of a gp120 core structure bound to CD4 has revealed an intervening β sheet (the "bridging sheet") between the inner and outer domains of gp120 that may serve as an additional contact site for the chemokine receptor (Wyatt and Sodroski, 1998, Science 280:1884–1888; Rizzuto et al., 1998, Science 280:1949–1953).

Although CD4 is generally required for gp120 to associate with a chemokine receptor, the identification of CD4-independent isolates of HIV-1, HIV-2, and SIV has demonstrated that functional interactions with chemokine receptors can occur in the absence of CD4 interaction (Edinger et al., 1997, Proc. Natl. Acad. Sci. USA 94:14742–14747; Reeves and Schulz, 1996, J. Virol. 71:1453–1465; Endres et al., 1996, Cell 87:745–756; Dumonceaux et al., 1998, J. Virol. 72:512–519). The determinants for the CD4-independent phenotype have been mapped to the viral env gene, but the underlying mechanisms of this phenotype are unknown. It has been proposed that mutations in env may increase the exposure and/or the affinity of the chemokine receptor binding site on gp120, thus circumventing the need for CD4 Endres et al., 1996, Cell 87:745–756).

Biochemical assays have also shown that mutated or deglycosylated recombinant gp120 can bind directly to chemokine receptors, suggesting that domains normally activated by CD4 can be artificially exposed (Hesselgesser et al., 1997, Curr. Biol. 7: 112–121; Martin et al., 1997, Science 278:1470–1473; Bandres et al., 1998, J. Virol. 72:2500–2504; Misse et al., 1998, J. Virol. 72:7280–7288). A greater understanding of the determinants responsible for CD4-independence should provide insights into the Env domains that mediate and modulate interactions of Env with chemokine receptors and that ultimately govern viral entry.

To date, the ability of HIV-1 to escape the immune system has hindered development of efficacious vaccines to this important human pathogen. Thus, there is a long-felt and unfilled need for the development of effective vaccines and therapeutic modalities for HIV-1 infection in humans. The present invention meets those needs.

BRIEF SUMMARY OF THE INVENTION

The invention includes an isolated nucleic acid encoding a CD4-independent human immunodeficiency virus-1 (HIV-1) env, or a mutant, derivative, or fragment thereof. In one aspect, the isolated nucleic acid shares at least about 98% homology with the nucleic acid having the nucleotide sequence of SEQ ID NO:4.

In another aspect, the nucleic acid is selected from the group consisting of an HIV-1/IIIBx env, and an HIV-1/IIIBx 8x (8x) env.

In yet another aspect, the nucleic acid is an HIV-1/IIIBx 8x env.

The invention also includes an isolated nucleic acid encoding a CD4-independent HIV env having the nucleotide sequence of SEQ ID NO:4.

The invention includes an isolated nucleic acid comprising a portion of a HIV-1 env gene which confers CD4 independence on at least one HIV-1 env clone.

The invention further includes a chimeric nucleic acid comprising a first portion and a second portion, the first portion encoding at least a portion of an HIV-1/IIIBx 8x env coding sequence and the second portion encoding at least a portion of an HIV-1 env coding sequence which is not an 8x env.

In one aspect, the second portion is an env coding sequence selected from the group consisting of an S10 env, an HXB2 env, a BaL env, and an IIIB env.

In another aspect, the second portion comprises a chemokine receptor binding site selected from the group consisting of a CXCR4 chemokine receptor binding site, and a CCR5 chemokine receptor binding site.

In yet another aspect, the second portion comprises a V3-loop coding sequence selected from the group consisting of a V3-loop for a CXCR4 chemokine receptor binding site, and a V3-loop for a CCR5 chemokine receptor binding site.

The invention includes an isolated HIV-1 gp120 polypeptide comprising a stably exposed chemokine coreceptor binding site.

The invention also includes an isolated polypeptide comprising an HIV-1/IIIBx 8x Env. In one aspect, the polypeptide shares at least about 98% homology with SEQ ID NO:3.

In another aspect, the isolated polypeptide comprises the amino acid sequence of SEQ ID NO:3.

The invention includes a chimeric HIV-1 Env polypeptide comprising a gp120 polypeptide wherein the chimeric polypeptide comprises a first portion comprising an HIV-1/IIIBx 8x gp120, the chimeric polypeptide further comprising a second portion comprising a gp120 from an HIV-1 other, than HIV-1/IIIBx 8x.

The invention further includes a chimeric HIV-1 Env polypeptide wherein the polypeptide is CD4-independent, and further wherein the polypeptide comprises a chemokine receptor binding site selected from the group consisting of a CXCR4 chemokine receptor binding site, and a CCR5 chemokine receptor binding site.

In one aspect, the second portion comprises a V3-loop selected from the group consisting of a HXB V3-loop, an 8x V3-loop, a BaL V3-loop, a YU-2 V3-loop, and an 89.6 V3-loop.

The invention includes a composition comprising a CD4-independent HIV-1 Env comprising a gp120 polypeptide comprising a stably exposed chemokine receptor binding site wherein the HIV-1 is more sensitive to antibody neutralization than an otherwise identical HIV-1 which does not comprise a stably exposed chemokine receptor binding site.

The invention also includes a pharmaceutical composition comprising a CD4-independent HIV-1 Env protein, wherein the HIV-1 Env comprises at least one mutation causing the chemokine coreceptor binding site to be stably exposed.

In one aspect, the HIV-1 Env is HIV-1/IIIBx 8x.

The invention includes a vaccine comprising an immunogenic dose of a CD4-independent HIV-1 Env.

In one aspect, the HIV-1 Env is selected from the group consisting of a HIV-1 Env polypeptide, a nucleic acid encoding HIV-1 Env, and a cell expressing HIV-1 Env.

The invention includes a vector comprising an isolated nucleic acid encoding a CD4-independent human HIV-1 env, or a mutant, derivative, or fragment thereof.

The invention also includes a vector comprising an isolated nucleic acid comprising a portion of a HIV-1 env gene which confers CD4 independence on at least one HIV-1 env clone.

The invention includes a vector comprising a chimeric nucleic acid comprising a first portion and a second portion, the first portion encoding at least a portion of an HIV-1/IIIBx 8x env coding sequence and the second portion encoding at least a portion of an HIV-1 env coding sequence which is not an 8x env.

The invention includes a cell comprising an isolated nucleic acid encoding a CD4-independent human HIV-1 env, or a mutant, derivative, or fragment thereof.

The invention also includes a cell comprising an isolated nucleic acid comprising a portion of a HIV-1 env gene which confers CD4 independence on at least one HIV-1 env clone.

The invention further includes a cell comprising a chimeric nucleic acid comprising a first portion and a second portion, the first portion encoding at least a portion of an HIV-1/IIIBx 8x env coding sequence and the second portion encoding at least a portion of an HIV-1 env coding sequence which is not an 8x env.

The invention includes a cell comprising an isolated HIV-1 gp120 polypeptide comprising a stably exposed chemokine receptor binding site.

The invention also includes a cell comprising an isolated polypeptide comprising an HIV-1/IIIBx 8x Env.

The invention includes a cell comprising a chimeric HIV-1 Env polypeptide comprising a gp120 polypeptide wherein the chimeric polypeptide comprises a first portion comprising an HIV-1/IIIBx 8x gp120, the chimeric polypeptide further comprising a second portion comprising a gp120 from an HIV-1 other than HIV-1/IIIBx 8x.

The invention also includes a cell comprising chimeric HIV-1 Env polypeptide wherein the polypeptide is CD4-independent, and further wherein the polypeptide comprises a chemokine receptor binding site selected from the group consisting of a CXCR4 chemokine receptor binding site, and a CCR5 chemokine receptor binding site.

In one aspect, the second portion comprises a V3-loop selected from the group consisting of a HXB V3-loop, an 8x V3-loop, a BaL V3-loop, a YU-2 V3-loop, and an 89.6 V3-loop.

The invention includes a cell comprising a composition comprising a CD4-independent HIV-1 Env comprising a gp120 polypeptide comprising a stably exposed chemokine receptor binding site wherein the HIV-1 is more sensitive to antibody neutralization than an otherwise identical HIV-1 which does not comprise a stably exposed chemokine receptor binding site.

The invention includes a method of identifying an amino acid residue of an HIV-1 Env protein which is involved in CD4 independence. The method comprises obtaining a full-length env coding sequence from an Env clone which is CD4-independent and replacing at least a portion of the said env coding sequence with a coding sequence from an Env clone which is CD4-dependent to form a chimera, wherein when the chimera is CD4-dependent it is an indication that the portion of the env coding sequence is involved in CD4-independence, thereby identifying an amino acid residue involved in CD4-independence.

The invention also includes a method of eliciting an immune response to a HIV-1 chemokine receptor binding site in a mammal. The method comprises administering an immunogenic dose of a CD4-independent HIV-1 Env protein to a mammal, wherein the protein comprises a stably exposed chemokine receptor binding site, thereby eliciting an immune response to a HIV-1 chemokine receptor binding site in a mammal.

The invention also includes a method of identifying a compound which affects exposure of an HIV-1 gp120 chemokine receptor binding site. The method comprises contacting a cell with the compound prior to or contemporaneous with contacting the cell with a labeled gp120 with or without pre-incubation of the gp120 with soluble CD4, measuring the amount of label bound to the cell, and comparing the amount of label bound to the cells contacted with the compound to the amount of label bound to otherwise identical cells not contacted with the compound, wherein a higher or lower amount of label bound to the cells contacted with the compound compared with the amount of label bound to the otherwise identical cells not contacted with the compound, is an indication that the compound affects exposure of an HIV-1 gp120 chemokine receptor binding site.

The invention includes a method of identifying a small-molecule which inhibits binding of an HIV-1 gp120, using its chemokine receptor binding site, to a chemokine receptor. The method comprises contacting a cell with the molecule prior to or contemporaneous with contacting the cell with labeled gp120 with or without pre-incubation of said gp120 with soluble CD4, measuring the amount of label bound to the cell, and comparing the amount of label bound to the cell contacted with the molecule with the amount of label bound to an otherwise identical cell not contacted with the molecule, wherein a lower amount of label bound to the cell contacted with the molecule compared with the amount of label bound to the otherwise identical cell not contacted with the molecule, is an indication that the molecule inhibits binding of an HIV-1 gp120 using its chemokine receptor binding site to a chemokine receptor.

The invention includes a method of producing a CD4-independent chimeric HIV-1 Env clone comprising a variable chemokine receptor binding site. The method comprises replacing the hypervariable V3-loop of the CD4-independent Env clone with the V3 loop of another HIV-1, wherein the V3-loop of another HIV-1 comprises a different chemokine receptor binding site than that of the CD4-independent Env clone.

In one aspect, the CD4-independent clone is selected from the group consisting of HIV-1/IIIBx, and HIV-1/IIIBx 8x.

In another aspect, the V3-loop from another HIV-1 is selected from the group consisting of a V3-loop from HIV-1/BaL, a V3-loop from HIV-1/YU-2, a V3-loop from HIV-1/ADA, and a V3-loop from HIV-1/89.6.

The invention also includes a method of inhibiting HIV-1 gp120 binding, using its chemokine receptor binding site, to a chemokine receptor. The method comprises contacting said gp120 with a small-molecule identified by a method of identifying a compound which affects exposure of an HIV-1 gp120 chemokine receptor binding site, the method comprising contacting a cell with the compound prior to or contemporaneous with contacting the cell with a labeled gp120 with or without pre-incubation of the gp120 with soluble CD4, measuring the amount of label bound to the cell, and comparing the amount of label bound to the cells contacted with the compound to the amount of label bound to otherwise identical cells not contacted with the compound, wherein a higher or lower amount of label bound to the cells contacted with the compound compared with the amount of label bound to the otherwise identical cells not contacted with the compound, is an indication that the compound affects exposure of an HIV-1 gp120 chemokine receptor binding site, thereby inhibiting HIV-1 gp120 binding, using its chemokine receptor binding site, to a chemokine receptor.

The invention includes a method of inhibiting HIV-1 infection of a cell. The method comprises contacting the cell with a small-molecule which inhibits binding of an HIV-1 gp120 using its chemokine receptor binding site to a chemokine receptor, wherein the small-molecule is identified using a method of identifying a small-molecule which inhibits binding of an HIV-1 gp120, using its chemokine receptor binding site, to a chemokine receptor, the method comprising contacting a cell with the molecule prior to or contemporaneous with contacting the cell with labeled gp120 with or without pre-incubation of said gp120 with soluble CD4, measuring the amount of label bound to the cell, and comparing the amount of label bound to the cell contacted with the molecule with the amount of label bound to an otherwise identical cell not contacted with the molecule, wherein a lower amount of label bound to the cell contacted with the molecule compared with the amount of label bound to the otherwise identical cell not contacted with the molecule, is an indication that the molecule inhibits binding of an HIV-1 gp120 using its chemokine receptor binding site to a chemokine receptor, thereby inhibiting HIV-1 infection of a cell.

The invention includes a composition comprising a CD4-independent HIV-1 Env and at least one compound used to treat HIV infection in a pharmaceutically suitable carrier.

In one aspect, the HIV-1 Env is selected from the group consisting of a HIV-1 Env polypeptide, a nucleic acid encoding HIV-1 Env, and a cell expressing HIV-1 env.

In another aspect, the compound used to treat HIV infection is selected from the group consisting of a protease inhibitor, a reverse transcriptase nucleoside analog inhibitor, a reverse transcriptase non-nucleoside analog inhibitor, an interferon, AZT, interleukin-2, and a cytokine.

The invention includes a method of treating HIV-1 infection in a human. The method comprises administering an immunogenic dose of a CD4-independent HIV-1 Env to an HIV-1 infected human, thereby treating HIV-1 infection in the human.

In one aspect, the HIV-1 Env is selected from the group consisting of a HIV-1 Env polypeptide, a nucleic acid encoding HIV-1 Env, and a cell expressing HIV-1 env.

In another aspect, the method further comprises administering a compound used to treat HIV infection.

In yet another aspect, the compound used to treat HIV infection is selected from the group consisting of a protease inhibitor, a reverse transcriptase nucleoside analog inhibitor, a reverse transcriptase non-nucleoside analog inhibitor, an interferon, AZT, interleukin-2, and a cytokine.

In a further aspect, the compound is administered to said human before, during or after administration of said CD4-independent HIV-1 Env.

BRIEF DESCRIPTION OF THE SEVERAL VIEWS OF THE DRAWINGS

FIG. 1A is a graph, comprising two panels, depicting viral replication in CD4-positive and CD4-negative T cells by HIV-1/IIIB or HIV-1/IIIBx. CD4-negative BC7 cells (top panel) and SupT1 CD4-positive cells (bottom panel) were inoculated with equal amounts of HIV-1/IIIB (open diamonds) or HIV-1/IIIBx (solid circles) and viral replication was determined by reverse transcriptase (RT) activity in culture supernatants.

FIG. 1B is a graph depicting the inhibition of HIV-1/IIIBx replication by anti-CXCR4 antibody (12G5). CD4-negative BC7 cells were inoculated with HIV-1/IIIBx in the absence (open bars) or presence (5 $\mu$g/ml, hatched bars, or 20 $\mu$g/ml, solid bars) of anti-CXCR4 antibody 12G5 and reverse transcriptase (RT) activity was determined at the time points indicated.

FIG. 1C is an image, comprising two panels, depicting cell fusion induced by HIV-1/IIIBx on murine cells expressing CXCR4. HIV-1/IIIBx-infected BC7 cells were co-cultured with murine 3T3 cells which do not express CXCR4 (3T3, left panel) or with 3T3 cells that express human CXCR4 (3T3/CXCR4, right panel) for 24 hours and then the cells were stained for syncytial formation as described in Endres et al. (1996, Cell 87:745–756).

Figure 2:
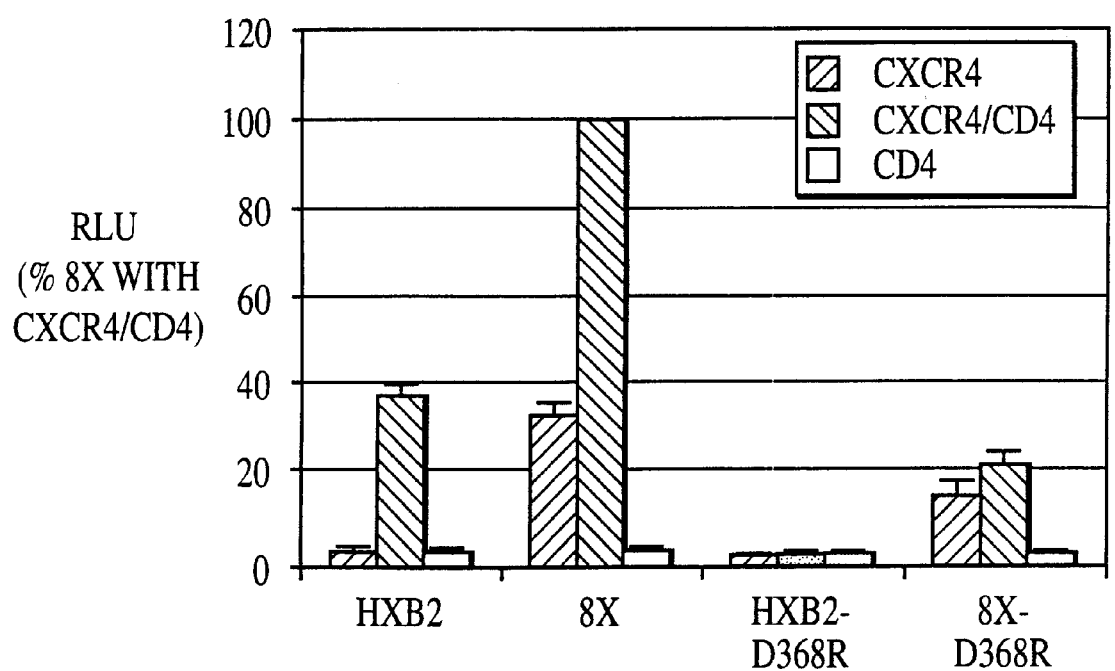

FIG. 2 is a graph depicting the fusion activity, expressed in relative light units (RLUs), of IIIBx env genes. The env genes indicated were cloned into pSP73, transfected into QT6 cells, and the genes were evaluated in fusion assays on QT6 cells expressing CD4 plus CXCR4, CXCR4 alone, or CD4 alone as described in Rucker et al. (1997, Methods Enzymol. 288:118–133) and as described elsewhere herein. The results are expressed as the mean+SEM in RLU normalized to the activity of 8x on CXCR4+/CD4+ cells. Also shown are the fusion activities for 8x and HXBc2 Envs containing a D368R mutation that ablates the CD4-binding site as described in Olshevsky et al. (1990, J. Virol. 64:5701–5705).

Figure 3A:
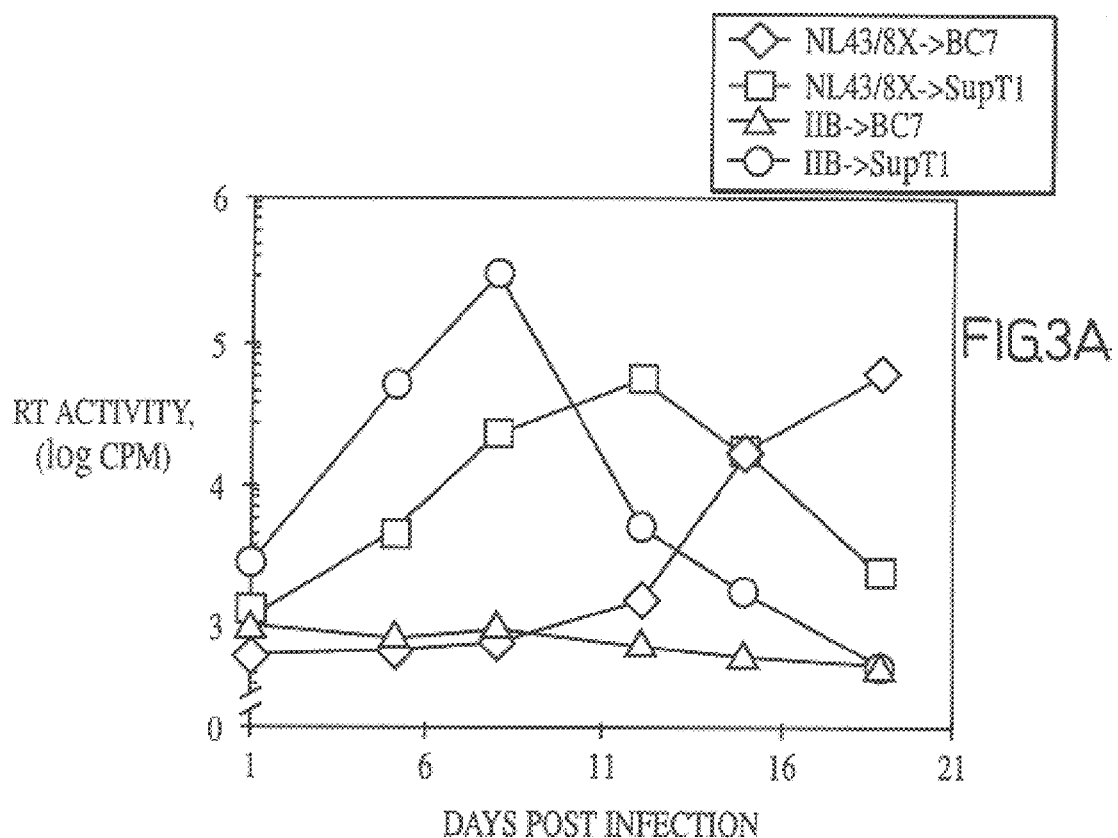

FIG. 3A is a graph demonstrating the fusion activity of the HIV-1/IIIBx env gene. The 8x env was inserted into pNL4-3 and a viral stock was generated after transfection of BC7 cells. Equal amounts of the resulting virus (designated NL43/8x) and HIV-1/IIIB were inoculated onto SupT1 and BC7 cells and RT levels were monitored over time.

Figure 3B:
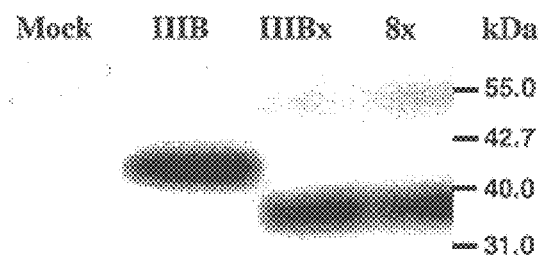

FIG. 3B is an image of a Western blot depicting the evaluation of the size of TM polypeptide of various viruses. Viral lysates from HIV-1/IIIB infected SupT1 cells (lane 1), IIIBx infected BC7 cells (lane 2), and NL43/8x-infected BC7 cells were evaluated by Western blot using anti-TM mouse monoclonal antibody D12. Consistent with the sequence analyses (FIG. 4), both IIIBx and NL43/8x exhibited a truncated TM protein.

Figure 4:
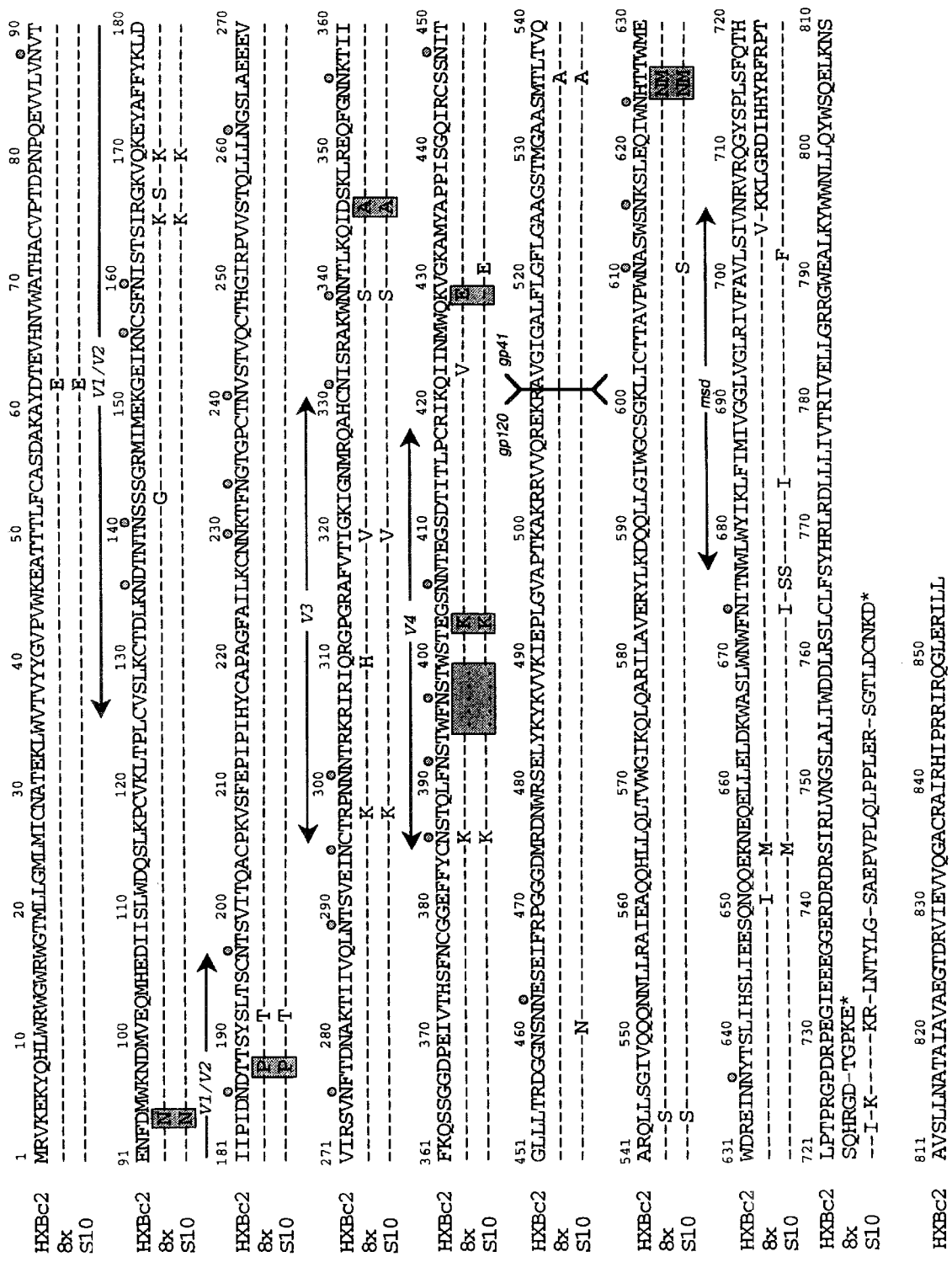

FIG. 4 is a diagram depicting the amino acid sequence analysis of IIIBx env clones. Sequence analysis for IIIBx env clones 8x (SEQ ID NO:3) and S10 (SEQ ID NO:12) are compared with that of HXBc2 (SEQ ID NO:11). The shaded regions indicate mutations that are also found in other clones from HIV-1/IIIB. The predicted N-linked glycosylation sites are indicated by the shaded gray circle symbol directly over the amino acid position (where amino acids are designated using a one-letter code). The positions of the variable loops, the gp120/gp41 cleavage site and the TM membrane spanning domain (msd) are also indicated above the amino acid sequence of HXBc2. The 8x sequence contains a frame shift mutation at amino acid position 706 which results in a prematurely truncated cytoplasmic tail compared with HXBc2. S10 contains a deletion of 50 nucleotides which also leads to a frameshift and a prematurely truncated cytoplasmic tail. In FIG. 4, dashes indicate amino acid residues that are identical to the corresponding amino acid residue of HXBc2.

Figure 5:
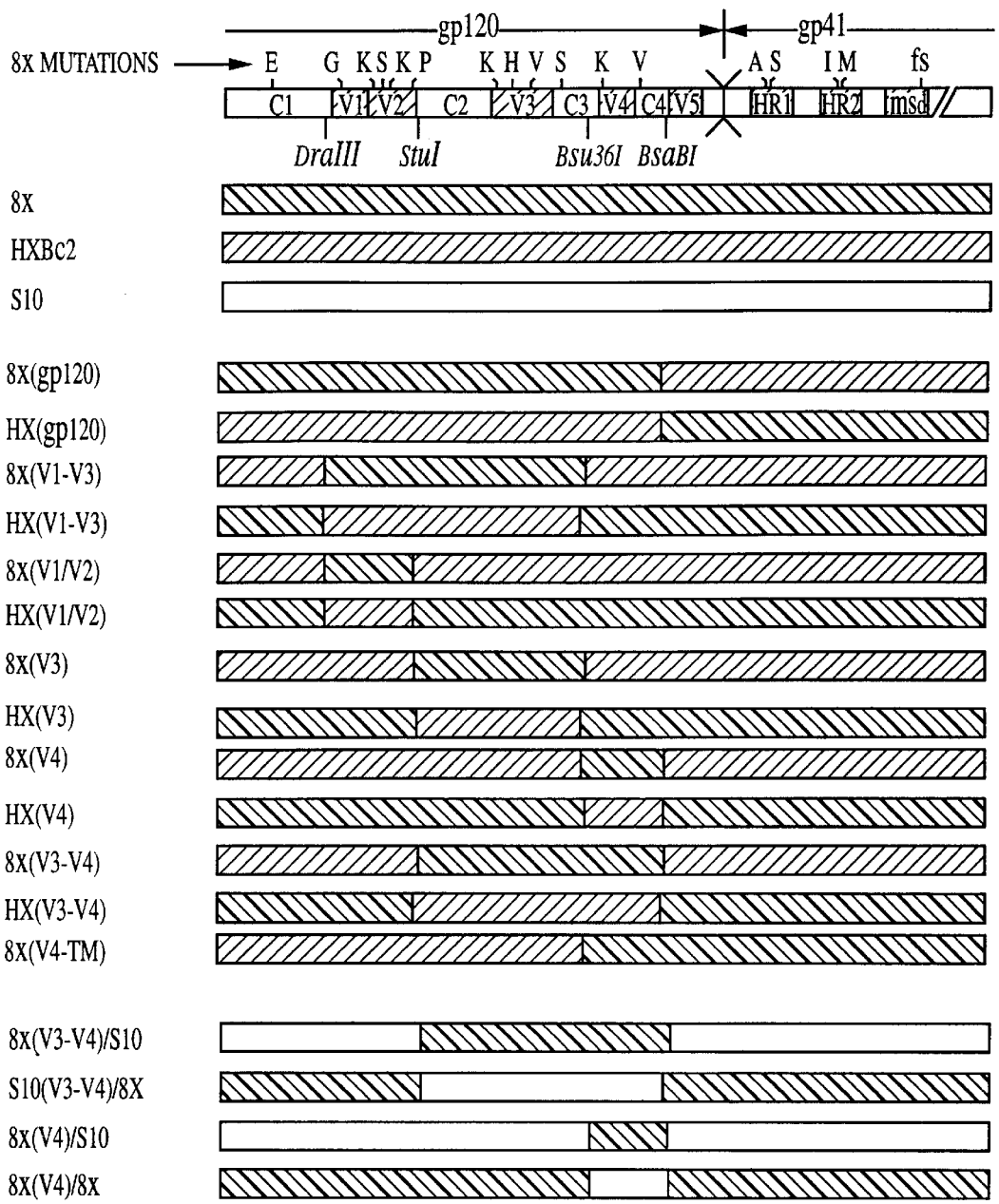

FIG. 5 is a diagram depicting the evaluation of chimeric Env proteins in fusion assays. The diagram depicts the env genes from 8x, S10, HXBc2, and chimeras constructed using the indicated restriction sites shown at the top of the diagram. The mutations present in 8x are indicated above the top schematic. The chimeras were cloned into pSP73 and evaluated in cell fusion assays as described in FIG. 6, infra.

Figure 6:
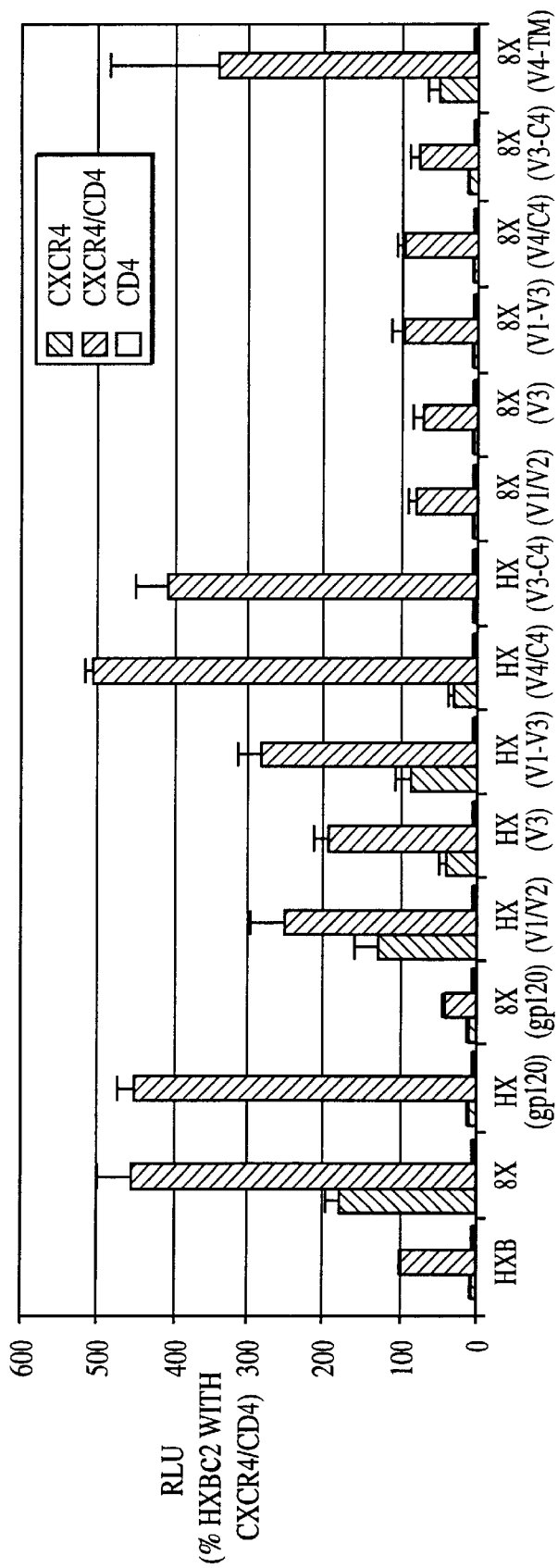

FIG. 6 is a graph depicting the evaluation of chimeric Env proteins in fusion assays. The chimeric Env proteins constructed between HXBc2 and 8x which are shown in FIG. 5, supra, were evaluated in fusion assays on QT6 target cells expressing CXCR4 alone, CXCR4 and CD4, or CD4 alone. The results are expressed as luciferase activity relative to that of HXBc2 on CXCR4+/CD4+ cells (i.e., relative luciferase units, RLU). The bars indicate the mean RLU for 3 experiments+SEM.

Figure 7:
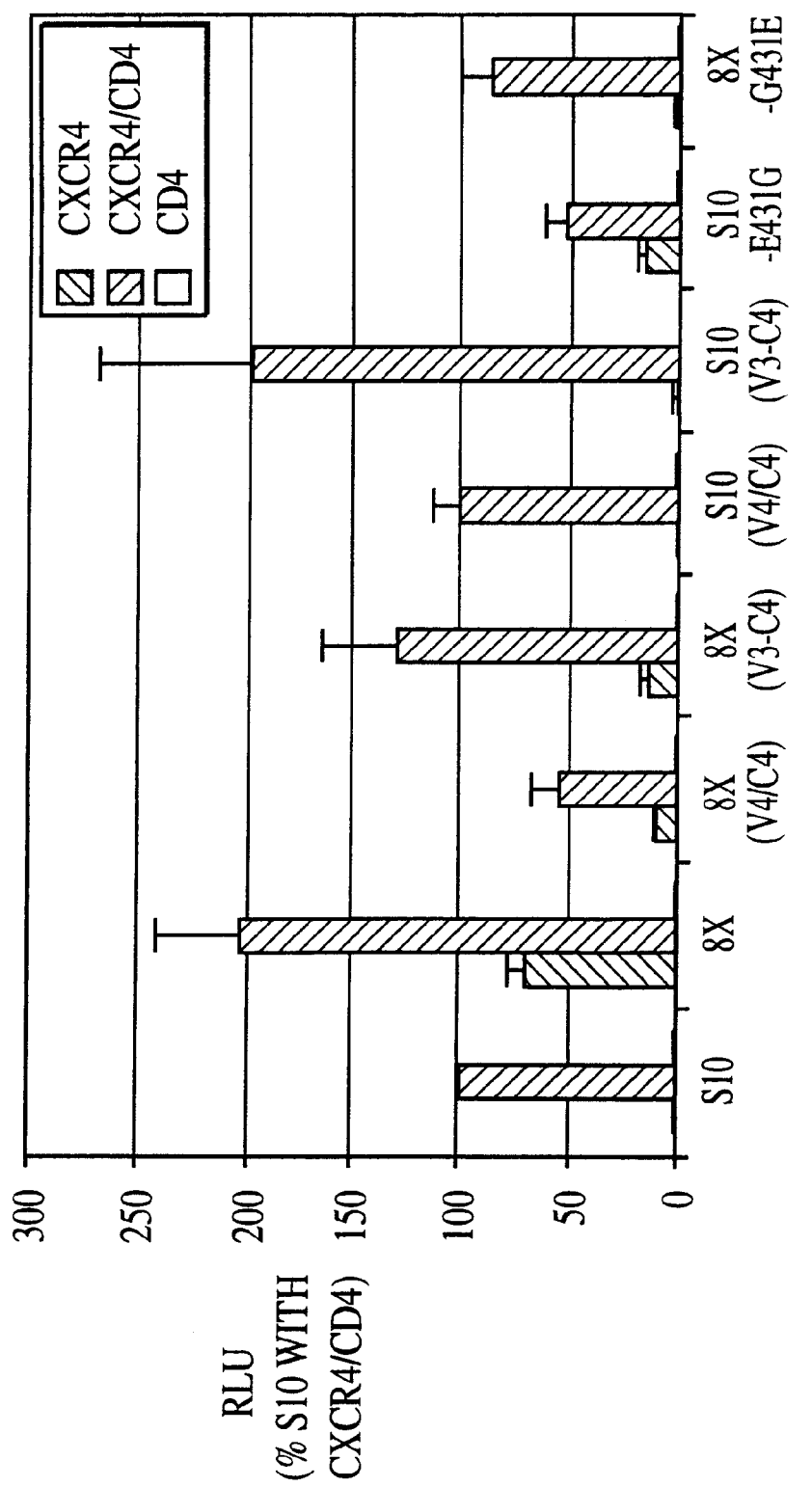

FIG. 7 is a graph depicting the mapping of determinants for a CD4-dependent clone of IIIBx. The fusion activity is shown for the CD4-dependent S10 clone of IIIBx and for S10/8x chimeras as indicated in FIG. 5, supra. In addition, the activity is shown for an S10 Env in which the G431E mutation in the C4 domain was corrected (S10-E431G) and for an 8x Env that contained this mutation (8x-G431E).

The results are expressed as the percentage of 8x luciferase activity on target cells that coexpressed CXCR4 and CD4.

Figure 8:
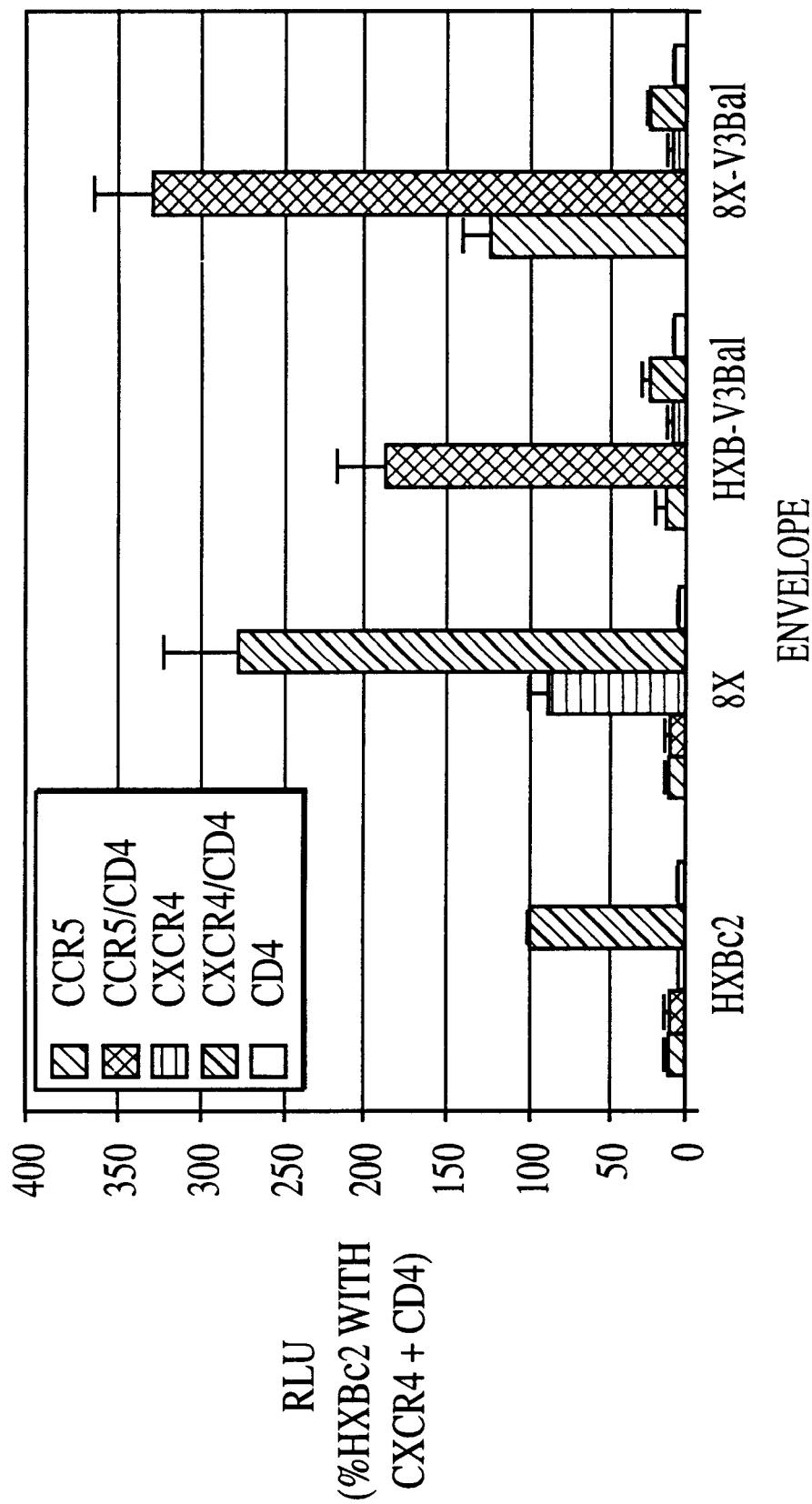

FIG. 8 is graph depicting the CCR5 tropism of Env proteins containing V3 loop from the CCR5-tropic Env, HIV-1/BaL. HXB2 (a molecular clone derived from the IIIB swarm) Env, which is CD4-dependent, and 8x Env proteins containing the V3 loop from HIV-1/BaL were constructed and their fusion activity was compared to the parental HBXc2 or 8x Envs on target cells that expressed CCR5 or CXCR4±CD4. Fusion activity is expressed as the percentage of luciferase activity of HXBc2 on target cells that expressed both CXCR4 and CD4. The bars indicate the mean+SEM.

Figure 9A:
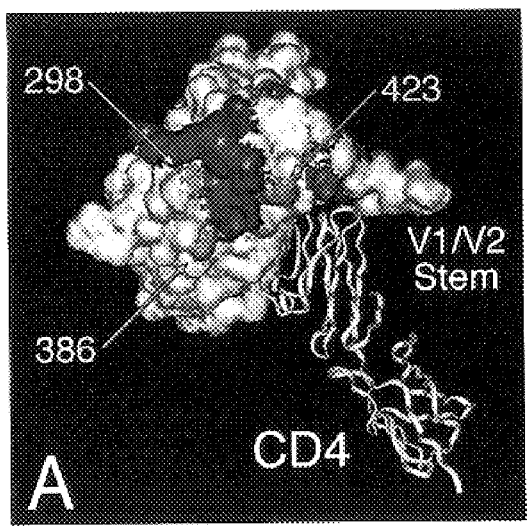

FIG. 9A is an image of a space-filling model depicting the HIV-1/HXB2 gp120 core crystal structure and demonstrating the location of HIV-1/IIIBx mutations on the gp120 crystal structure. The core crystal structure is depicted in white in conjunction with a ribbon diagram of CD4 (Kwong et al., 1998, Nature 393:648–659) which is shown in the bottom right quadrant of the image. The amino acid sites at which mutations produced a 50% decrease or increase in gp120 binding to CCR5 (Rizzuto et al., 1998, Science 280:1949–1953) are shown in red. Without wishing to be bound by theory, of the 6 mutations in 8x that could be mapped onto the gp120 core, 3 (shown in light blue) are located immediately adjacent to this putative chemokine receptor binding site.

Figure 9B:
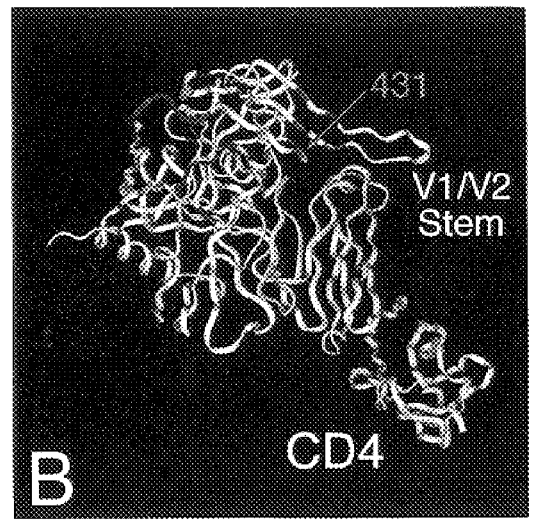

FIG. 9B is an image of a ribbon diagram of the gp120/CD4 complex depicted in a slightly different orientation from that shown in FIG. 9A, supra, in order to indicate the position of the G431E mutation, which was sufficient to abrogate CD4-independence but not CD4-dependent fusion of the 8x clone.

Figure 10B:
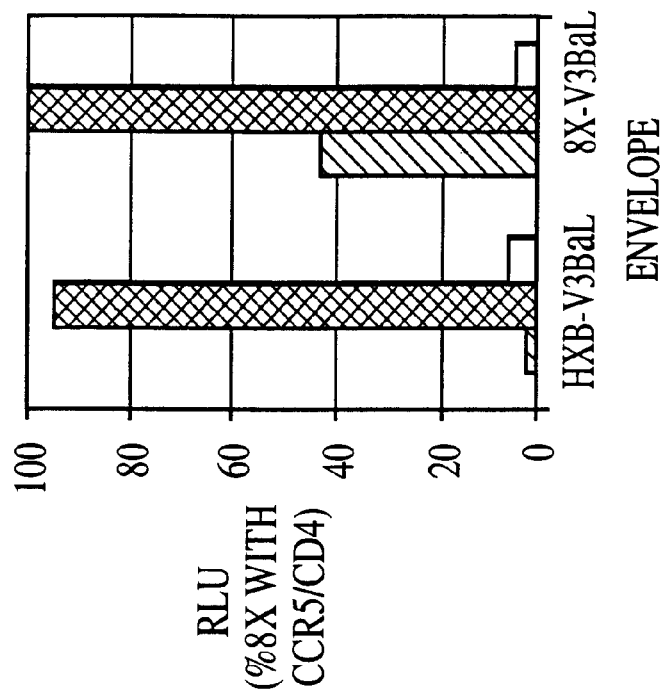
Figure 10A:
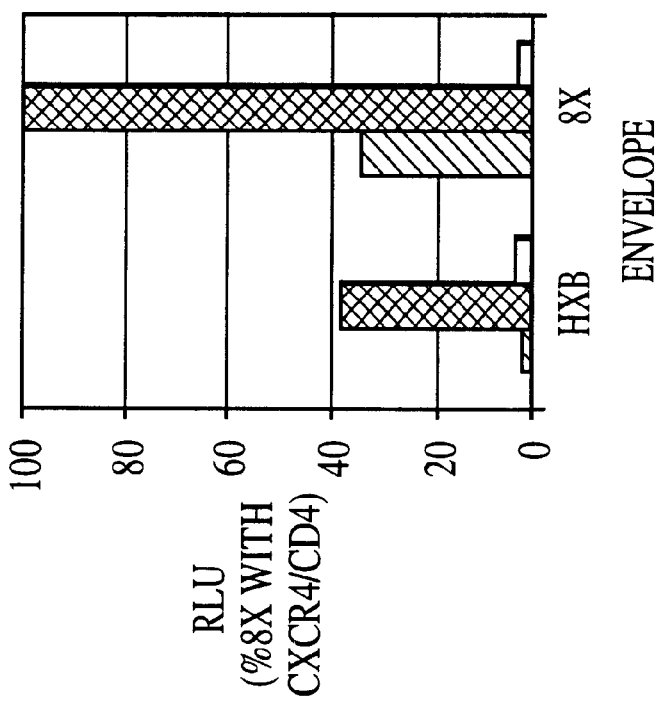

FIG. 10A is a graph depicting CD4-independent cell-cell fusion by HXB or 8x Env clones. QT6 effector cells expressing HXB or 8x Env, as indicated, as well as T7 polymerase were mixed with QT6 target cells expressing chemokine receptor CXCR4 (cross-hatched bars), CD4 (open bars), or CXCR4/CD4 (closed bars) and the luciferase gene under control of the T7 promoter. HIV-1/IIIB is an uncloned virus from which several molecular clones, such as HXBc2 ("HXB") and IIIBx ("8x"), have been derived. The data disclosed herein compare these two Env molecular clones. Luciferase is produced in this assay only if Env mediates fusion between effector and target cells. The results for each Env are expressed in RLUs and are normalized to the amount of fusion obtained with IIIB Env effector and CXCR4/CD4 target cells. The results of a typical experiment are shown.

FIG. 10B is a graph depicting CD4-independent cell-cell fusion by HXB-V3BaL or 8x-V3BaL Env clones. Luciferase reporter viruses bearing HXB-V3BaL or 8x-V3BaL Env proteins, as indicated, were used to infect 293T cells expressing CCR5 (cross-hatched bars), CD4 (open bars), or CCR5/CD4 (gray bars) and the luciferase gene under control of the T7 promoter. The amount of luciferase activity was determined 3 days after infection. The results for each Env are expressed in RLU and are normalized to the results obtained with virions bearing the IIIB-BAL Env and CCR5/CD4 target cells. The results of a typical experiment are shown.

Figure 11:
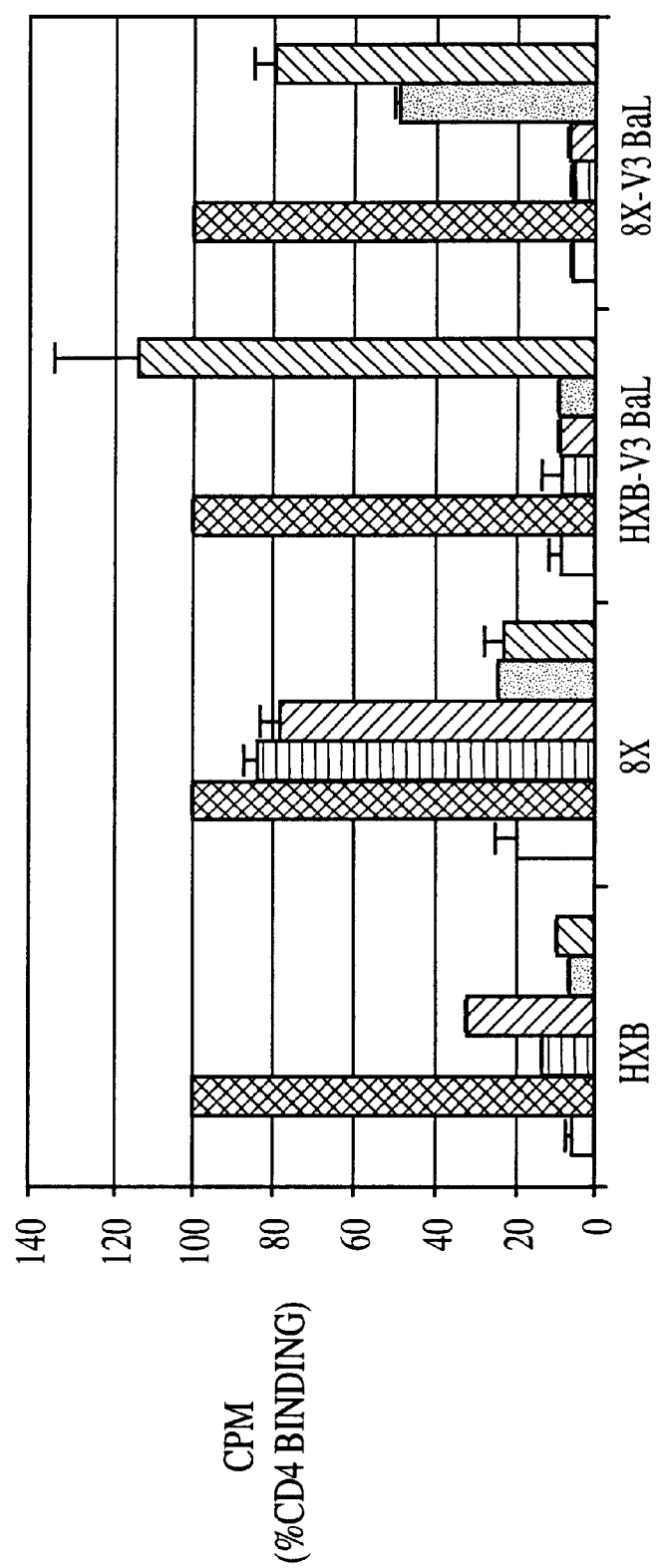

FIG. 11 is a graph depicting cell-surface binding of various gp120s in cells expressing CD4, CXCR4 or CCR5. Radioiodinated gp120s were incubated with 293T cells transiently transfected with coreceptor or CD4 plasmids. Soluble CD4 (sCD4) was added to the binding reaction as indicated. The amount of specific radioactivity bound to the cells is presented and is normalized for each gp120 indicated such that binding to CD4 represents 100%. Each value represents the average of $\geq 3$ independent experiments and the error bars represent SEMs. The following combinations are shown: cells expressing empty vector pCDNA3 (open bars), cells expressing CD4 (solid bars), cells expressing CXCR4 (dark -gray bars), cells expressing CXCR4 with sCD4 added (dark cross-hatch bars), cells expressing CCR5 (light gray bars), cells expressing CCR5 with sCD4 added (light cross-hatch bars).

Figure 12:
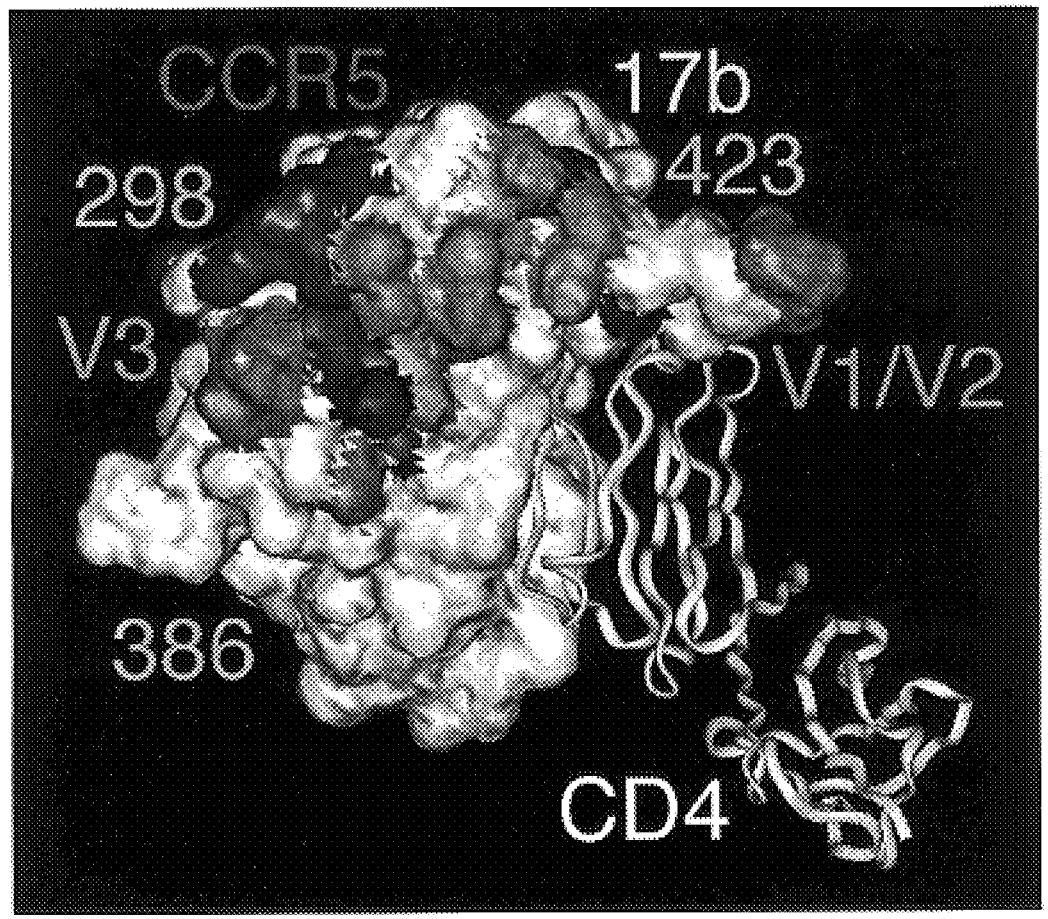

FIG. 12 is an image of a space-filling model of gp120 bound to CD4 depicting the overlap between the CCR5 coreceptor binding site and the MAb 17b epitope. The amino acid residues shown by Rizzuto et al. (1998, Science 280:1949–1953), to decrease CCR5 binding by greater than 50% when mutated while reducing CD4 binding by less than 50% are shown in red. The contact residues for MAb 17b are shown in light blue, and the residues involved in both CCR5 and 17b binding are shown in lavender. Three residues that differ between 8x and IIIB in the vicinity of the coreceptor binding site as disclosed previously in Example 1 and which may impact CD4-independence, are shown in green. One of these residues, 423, is also a contact site for MAb 17b. The stems of the hypervariable V1/V2 and V3 loops are shown in orange.

Figure 13:
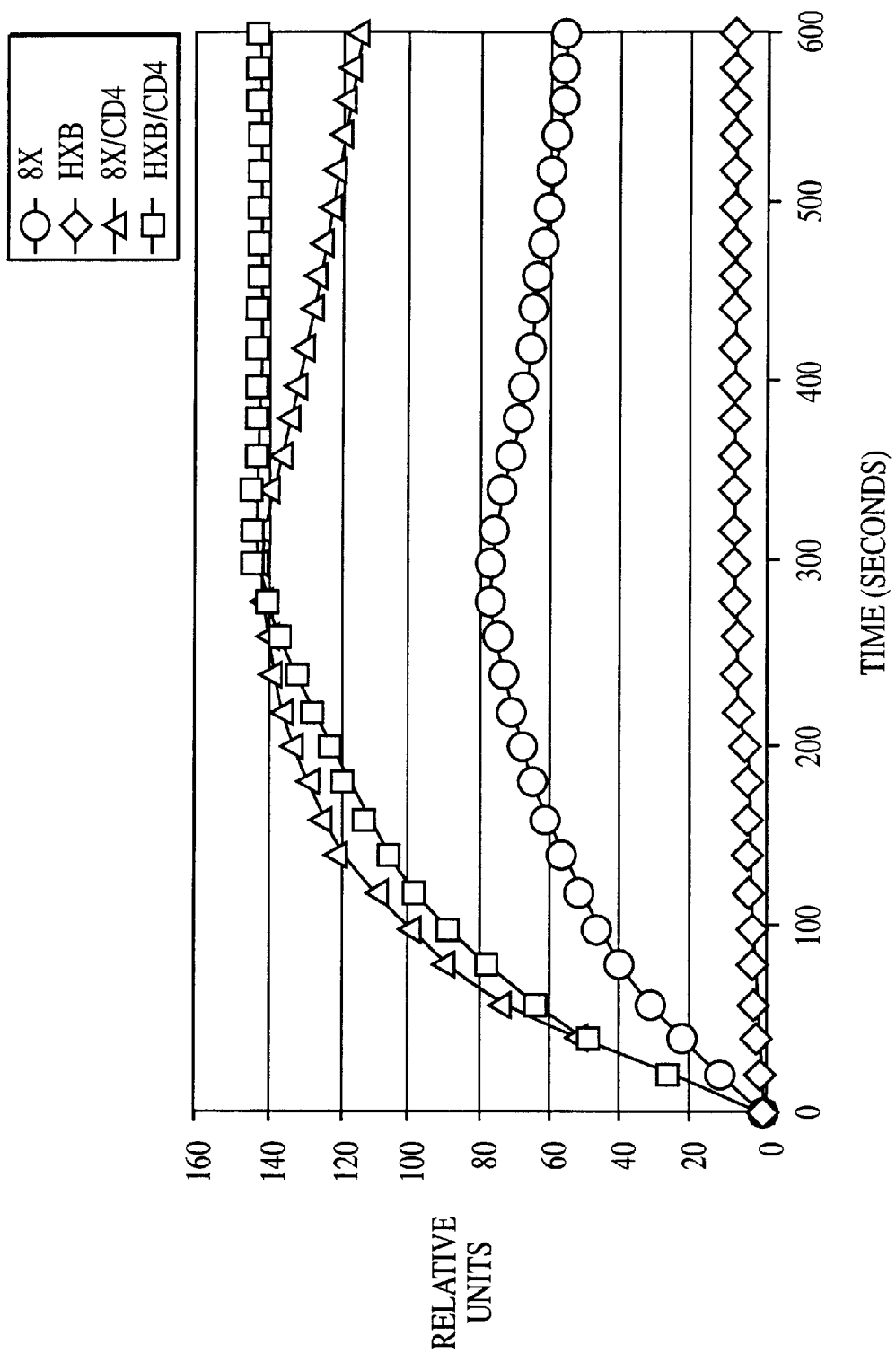

FIG. 13 is a graph depicting the sensorgrams for gp120 binding to the CD4i MAb 17b. MAb 17b was attached to the sensor surface after which the indicated gp120 molecule (at equal concentrations), with or without prior incubation with saturating levels of sCD4 as indicated, were applied to the flow cell. A 300 second association was followed by a wash with running buffer for an additional 300 seconds during which dissociation was measured. The kinetic constants derived from linear transformations of the data are presented in Table 1 elsewhere herein.

FIG. 14, comprising FIGS. 14A and 14B, lists the nucleotide sequence of env obtained from clone 8x.

DETAILED DESCRIPTION OF THE INVENTION

The invention is based on the discovery of a CD4-independent variant of HIV-1/IIIB, designated HIV-1/IIIBx (IIIBx), and a functional full-length env clone therefrom termed HIV-1/IIIBx.8 (8x), which allow the study of the mechanism for virus infection of host cells involving cell receptor proteins. Further, the present invention relates to the construction of chimeras comprising portions of a nucleic acid encoding 8x env covalently linked to a least one nucleic acid encoding a portion of an env from another HIV-1 virus. Thus, the chimeras are produced by combining portions of the 8x env coding sequence with portions of the env coding sequences of other virions leading to the further discovery of which portion(s) of the 8x HIV-1 env sequence is involved in CD4-independence.

CD4-independence is important in that it is an indicator that the chemokine binding site of gp120 is stably exposed on the virus envelope and is capable of binding to the cellular chemokine receptor binding protein without prior binding of the gp120 to CD4. Typically, the chemokine binding site is hidden until such binding to CD4 causes a conformational change exposing the site and resulting in a "triggered" conformation capable of binding to the chemokine receptor protein on the host cell. Therefore, the CD4-independent gp120 represents a stable intermediate configuration which may be used to, inter alia, identify the protein determinants involved in gp120 binding to a chemokine receptor protein, produce neutralizing antibodies capable of recognizing the gp120 chemokine receptor binding site, and to identify small-molecule inhibitors which can block gp120/chemokine receptor binding.

Accordingly, understanding which portions of the Env are involved in virus binding to cell proteins and thereby mapping the protein determinants involved in HIV-1 virus binding to host cell receptors is important in the development of effective antiviral vaccines to viral protein domains crucial for virus infection. Such domains are believed to be highly conserved but somehow "camouflaged" from the immune system such that a protective immune response is not mounted to such protein domains. Therefore, identification of these protein domains and the ability to present them to the immune system such that an immune response is generated to HIV-1 is an important goal of vaccine development to this important human pathogen.

Moreover, production of chimeras has led to the discovery that the CD4 dependence trait and the choice of chemokine receptor are functionally dissociable traits. One skilled in the art would appreciate, based upon the disclosure provided herein, that such chimeras are useful for mapping the various structural and functional elements of the nucleic acid encoding env and the Env protein encoded thereby. Thus, by combining various portions of different viruses having different properties, e.g., CD4-dependence or independence and/or different affinities for various chemokine receptors, the various functional elements of the Env protein may be examined and identified.

In one embodiment, replacing the V3-loop portion of 8x gp120, which binds the CXCR4 chemokine receptor in the absence of CD4, with the V3-loop of HIV-1/BaL, which is a virus strain that is CD4-dependent and binds the CCR5 chemokine coreceptor, converts the chimeric gp120 8x/V3-BaL to a CCR5 binding protein which retains CD4-independence. This further demonstrates that CD4-independence exposes the chemokine receptor binding domain such that the preceding step of CD4-binding by gp120 is no longer required regardless of the choice of chemokine receptor. These data also suggest that a chemokine receptor binding site exists on the gp120 that is able to interact with genetically divergent chemokine receptors (i.e., CXCR4 and CCR5) and this site is functional and likely exposed on CD4-independent viruses.

In addition, the present invention teaches that the CD4-independent gp120 protein exists in a stable partially "triggered" state, wherein the chemokine coreceptor binding site is more exposed in the CD4-independent gp120 protein than in the CD4-dependent conformation of the HIV-1 gp120 molecule. This has the effect of rendering the CD4-independent virus more susceptible to neutralization by anti-HIV-1 antibodies from mouse, human and rabbit. Therefore, the present invention has important implications for the development of HIV-1 therapeutics since the availability of a stably exposed, highly conserved chemokine receptor binding site, which may be otherwise camouflaged to escape immune detection, should facilitate the development of a humoral and/or cellular immune response and of small-molecule inhibitors to block this virus-host protein interaction, thereby preventing HIV-1 infection.

The present invention includes an isolated nucleic acid encoding a CD4-independent HIV env coding sequence which is comprised of two components, a portion encoding gp120 and a portion encoding gp41. In one embodiment, the full-length env clone of CD4-independent HIV-1/IIIBx, i.e., 8x, has been isolated (SEQ ID NO:3 and SEQ ID NO:4; see FIGS. 3 and 14A and 14B, respectively). Further, the mutations in the 8x clone were identified relative to the known env coding sequence of HXBc2 (GenBank Accession No. AF038399) (SEQ ID NO:11) and are disclosed in FIG. 4. However, the present invention should not be construed to be limited to a full-length env clone of the CD4-independent HIV-1/IIIBx variant. Rather, the present invention should be construed to encompass partial env clones. Indeed, the data disclosed herein demonstrate that the entire env coding sequence of 8x is not required for CD4-independence. Thus, at least one mutation present in the 8x env coding sequence confers CD4-independence to 8x, but not all mutations in the clone are required for purposes of the present invention. Further, completely separate mutations of gp120 can also confer CD4-independence.

The experiments disclosed in the Examples below disclose the isolation of a CD4-independent strain of the invention, HIV-1/IIIBx, which was able to infect both CD4$^+$ SupT1 cells and CD4$^-$ BC7 cells, a SupT1 variant, as demonstrated by a reverse transcriptase activity assay (FIG. 1A). However, the present invention is not limited solely to infection of BC7 or SupT1 cells by HIV-1. Rather, the "CD4-independence" of the present invention encompasses infection by HIV-1 of any cell type which does not express CD4. Further, as discussed previously herein, a CD4-independent HIV-1 strain may also infect cells that are CD4$^+$ although CD4/gp120 interaction is not required for infection of these cells by the CD4-independent HIV-1. Moreover, a CD4-independent HIV-1 strain need not infect every CD4$^-$ cell type. Rather, the HIV-1 strain need only be able to infect at least one CD4$^-$ cell type while its otherwise identical parental strain from which the clone was obtained cannot infect that cell type.

Additionally, for purposes of the invention, an HIV-1 strain variant is considered CD4-independent when it is able to infect at least about 5% of the susceptible cells in culture or the level of infection is about two to three-fold compared to background levels.

It will be appreciated by one skilled in the art, based upon the disclosure provided herein, that a CD4-independent isolate of an HIV-1 strain may be obtained by passaging a CD4-dependent HIV-1 swarm initially grown in CD4$^+$ cells onto cells which are CD4$^-$. As disclosed in the experiments described in Example 1 herein, HIV-1/IIIBx was obtained by passaging virus in CD4$^+$ SupT1 cells followed by passaging virus on the otherwise identical but CD4$^-$ BC7 cells. However, the invention should not be construed to be limited to these particular cell types. Instead, the invention encompasses a variety of CD4$^+$ and CD4$^-$ cells including, but not limited to, 293, Cf2TH, CCC$^+$L$^-$, and QT6 cells as well as stably transfected cells (U87, HeLa, HOS) that express a recombinant chemokine receptor in the presence or absence of CD4.

In other related aspects, the invention includes vectors which contain such an isolated nucleic acid comprising at least a portion of the HIV-1 env and which isolated nucleic acid is preferably capable of directing expression of the protein encoded by the nucleic acid; and virions, proviruses, and/or cells containing such vectors.

As the present experimental examples demonstrate, the nucleic acid encoding the Env protein may be cloned into various plasmid vectors. However, the present invention should not be construed to be limited to these plasmids or to any particular vector. Instead, the present invention should be construed as encompassing a wide plethora of vectors which are readily available and/or well-known in the art. Therefore, although in one embodiment, the full-length env coding regions were amplified by PCR and cloned into the plasmid pCDNA3, and the inserts were then sub-cloned into the 3' hemigenome of pNL4-3, the present invention should not be construed to be limited to these, or to any other, specific vectors.

The isolated nucleic acid of the invention should be construed to include an RNA or a DNA sequence encoding an Env protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention also includes an isolated polypeptide comprising the amino acid sequence of HIV-1/IIIBx 8x.

The present invention also provides for analogs of proteins or peptides which comprise a gp120 protein as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, carboxylation, or biotinylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Further, the invention should be construed to include naturally occurring variants or recombinantly derived mutants of HIV-1/IIIBx 8x env sequences, which variants or mutants render the protein encoded thereby either more, less, or just as biologically active as the full-length 8x env clone of the invention.

In addition, the present invention includes mutants or variants of 8x gp120 comprising an altered chemokine receptor binding site. As discussed previously elsewhere herein, the gp120 protein comprises a chemokine receptor binding domain which mediates gp120 binding to various cellular chemokine receptor proteins, which binding typically occurs after gp120 binding to CD4. As disclosed in the experimental results which follow this section, 8x gp120 binds to CXCR4 chemokine receptor and does not require binding to CD4 before doing so. Further, the data disclosed elsewhere herein demonstrate that introduction of a portion of a nucleic acid encoding a portion of an HIV-1/BaL gp120 into the coding sequence of 8x gp120 gives rise to a chimeric protein that no longer binds to CXCR4. Instead, the chimeric gp120 now binds CCR5. Such mutants are useful in the methods of the invention for the study of the role of gp120-chemokine receptor protein interaction in HIV-1 virus infection. The present invention should not be construed to be limited solely to a chimeric gp120 wherein a portion of the nucleic acid encoding 8x gp120 has been replaced a portion of a nucleic acid encoding BaL gp120. Instead, the present invention should be construed to include other chimeras wherein any portion or portions of the nucleic acid encoding 8x gp120 may be replaced by at least one portion of a nucleic acid encoding a gp120 from any other HIV-1 strain, preferably, those strains of HIV (or SIV) that use CCR5 as a coreceptor. Further, such portions should not be construed as being limited to any particular domain of gp120, but rather, the portion of gp120substituted may be from any portion of the sequence encoding the protein. Therefore, the resulting chimeric nucleic acid and the protein expressed therefrom may be a chimera comprised of various gp120s from several HIV-1 strains, in any combination possible.

As more specifically set forth elsewhere herein, a mutant gp120 gene which encodes a gp120 protein comprising an insertion, deletion, or substitution, whereby amino acids residues at or near the putative chemokine receptor binding site are altered, or whereby a truncated cytoplasmic tail of Env is produced, is useful in studying the association of gp120 with a host cell chemokine receptor protein. Indeed, as disclosed in the experiments described below, several such mutants have been discovered herein (see Table 1 and FIG. 3). However, the invention should not be construed as being limited to only these mutants; rather, the invention encompasses other mutants, comprising deletion, substitution, and point mutations, which demonstrate altered binding to chemokine receptor protein compared with the wild type gp120 and which mutants demonstrate CD4-independence.

The invention should also be construed to include DNA encoding variants of HIV-1Env which may or may not retain biological activity. Such variants, i.e., analogs of proteins or polypeptides of gp120, gp41 (also referred to as TM), include proteins or polypeptides which have been or may be modified using recombinant DNA technology such that the protein or polypeptide possesses additional properties which enhance its suitability for use in the methods described herein, for example, but not limited to, variants conferring enhanced stability of the exposed chemokine receptor binding site, enhanced specific binding to CD4, CXCR4, CCR5, and the like.

The present invention includes analogs of the 8x Env protein. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function.

Preferably, the amino acid sequence of an 8x Env analog is about 70% homologous, more preferably about 80% homologous, even more preferably about 90% homologous, more preferably, about 95% homologous, and most preferably, at least about 99% homologous to the amino acid sequence of 8x env (SEQ ID NO:3) disclosed herein at FIG. 4.

The invention should not be construed as being limited solely to the DNA and amino acid sequences disclosed herein. Once armed with the present invention, it is readily apparent to one skilled in the art that other CD4-independent env clones of HIV-1 may be obtained by following the procedures described herein in the experimental details section for the isolation of the 8x env nucleic acid (SEQ ID NO:4) encoding CD4-independent Env disclosed herein.

The invention should therefore be construed to include any and all nucleic acid sequences encoding HIV-1/IIIBx 8x Env and amino acid sequences having substantial homology to the nucleic acid encoding 8x env disclosed herein (SEQ ID NO:4) and the amino acid sequence (SEQ ID NO:3) shown in FIG. 4. Preferably, DNA which is substantially homologous is about 50% homologous, more preferably about 70% homologous, even more preferably about 80% homologous and most preferably about 90% homologous to the 8x env sequence (SEQ ID NO:4) disclosed herein. Preferably, an amino acid sequence which is substantially homologous is about 50% homologous, more preferably about 70% homologous, even more preferably about 80% homologous and most preferably about 90% homologous to the 8x Env amino acid sequences (SEQ ID NO:3) shown in FIG. 4.

Any number of procedures may be used for the generation of mutant or variant forms of 8x env. For example, generation of mutant forms of 8x which are not CD4 independent was accomplished herein by introducing portions of a nucleic acid encoding env from a virus which was CD4-dependent using recombinant DNA methodology well known in the art such as, for example, as described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). Mutant Env so generated is expressed and the resulting protein is assessed for its ability to bind CD4 in a real time biosensor assay such as that described herein. Mutant proteins which bind chemokine receptor protein in a CD4-independent manner were then examined by RT, fusion activity, real time binding/dissociation kinetics, and other such assays.

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention also includes an isolated nucleic acid having nucleic acid sequence which is complementary to a portion or all of the nucleic acid encoding HIV-1Env (SEQ ID NO:4).

As used herein, the term "fragment" as applied to a nucleic acid, may ordinarily be at least about 100 nucleotides in length, typically, at least about 200 nucleotides, more typically, from about 300 to about 600 nucleotides, typically at least about 700 to about 1000 nucleotides, preferably at least about 1000 to about 1400 nucleotides, even more preferably at least about 1600 nucleotides to about 2000 nucleotides, and most preferably, the nucleic acid fragment will be greater than about 2400 nucleotides in length.

The invention further includes a cell comprising the nucleic acids of interest. The nucleic acids need not be integrated into the cell genome nor do they need to be expressed in the cell. Moreover, the cell may be a prokaryotic or a eukaryotic cell and the invention should not be construed to be limited to any particular cell line or type.

The invention also includes antibodies specific for the chemokine receptor binding site of gp120, or a portion thereof, which antibodies comprise a monoclonal antibody.

In one embodiment, the antibody is a murine monoclonal antibody to gp120 (17b) the epitope of which overlaps with the chemokine receptor binding site, as well as a murine monoclonal antibody to gp120 termed 48d (Thali et al., 1993, J. Virol. 67:3978–3988). However, the invention should not be construed as being limited solely to these antibodies but rather, should be construed to include other antibodies, as that term is defined herein, to Env, or portions thereof, which antibodies perform in a manner substantially similar to those described herein in that, inter alia, the antibodies bind to gp120 chemokine receptor binding site, and they are able to inhibit HIV- 1 infection as measured by RT activity and cell fission activity.

The invention also comprises an isolated polypeptide comprising the amino acid sequence of 8x Env protein, and mutants, variants and fragments thereof.

The peptides of the invention may be substantially pure. A substantially pure peptide is purified by following known procedures for protein purification, wherein an immunological, enzymatic or other assay is used to monitor purification at each stage in the procedure. Protein purification methods are well known in the art, and are described, for example in Deutscher et al. (1990, In: Guide to Protein Purification, Harcourt Brace Jovanovich, San Diego).

The invention should thus be construed to include nucleic acid encoding desired proteins and fragments of nucleic acid encoding desired polypeptides.

The present invention includes an isolated nucleic acid encoding a chimeric protein comprising a first portion and a second portion. In one embodiment, the chimeric nucleic acid comprises a first portion encoding 8x env and a second portion encoding an env from S10, IIIB, or HXB2. Although these chimeras were useful in mapping which regions of 8x are required for CD4-independence, the present invention should not be construed to be limited to these chimeras. Rather, the invention should be construed to encompass any chimeras in the env coding region which may be constructed comprising any portion of 8x and any HIV-1 virus strain or variant thereof.

Further, in another embodiment, the chimeras comprised a portion of the 8x env coding region and a portion of the env coding region of a CCR5-tropic HIV-1 strain, BaL. More specifically, the embodiment comprises the 8x env clone with the nucleic acid portion encoding the V3-loop of BaL. However, the present invention should not be construed to be limited to this particular portion of the env coding region or to this particular strain of HIV-1. Rather, as previously discussed elsewhere herein, the present invention includes the substitution of any portion of the 8x env coding sequence with a portion of the env coding sequence of at least one other HIV-1 strain or variant, and any possible permutation thereof. Therefore, the chimeras, both nucleic acid and amino acid expressed therefrom, include combinations from two or more HIV-1 env coding regions of interest. Thus, armed with the disclosure provided herein, the production of an almost infinite combination of chimeras with the predicted effects disclosed herein would be clear to one skilled in the art.

The invention also includes a method of identifying an amino acid residue of an HIV-1Env protein which is involved in CD4-independence. The method comprises producing chimeric proteins comprising at least a portion from a CD4-independent Env clone and at least a second portion from a CD4-dependent Env clone. The resulting chimera is then examined to determine the ability of the chimeric protein to mediate CD4-independent infection by various assays as disclosed elsewhere herein. As discussed previously herein, a preferred embodiment is disclosed wherein portions of the 8x env coding sequence were combined with various portions of the env coding sequences of several CD4-dependent HIV-1 strains, e.g., S10 and HXBc2. Also as noted previously herein, the present invention is not limited to these particular combinations or to these particular strains. Rather, one skilled in the art would appreciate, based on the disclosure provided herein, that any combination of CD4-dependent and -independent env coding sequences may be examined to map the CD4-independent determinants. Further, the CD4-independence may be examined using a variety of assays on various mammalian cell lines also as described previously elsewhere herein.

The present invention also includes an isolated gp120 protein comprising a stably exposed chemokine receptor binding site. In one embodiment, the increased exposure of the chemokine receptor binding site was determined by measuring the real time binding kinetics of the various proteins in biosensor experiments and the enhanced neutralization of the virus by anti-HIV antibodies and by crystallographic analyses. However, the present invention should not be construed to be limited to these particular assays. Rather, other assays well-known in the art or to be developed for the study of protein-protein interactions may be used to measure the exposure of the chemokine receptor binding site of a gp120 or Env protein of interest.

The invention includes a method of eliciting an immune response to a HIV-1 chemokine receptor binding site. The method comprises administering an immunogenic dose of a CD4-independent HIV-1 Env protein to a mammal wherein the protein comprises a stably exposed chemokine receptor binding site.

In addition, the use of purified nucleic acid to generate an immune response, where the nucleic acid is in a vector (e.g., a plasmid or a virus), or where the nucleic acid comprises naked nucleic acid not associated with any other nucleic acid, is well-known in the art. For example, methods for construction of nucleic acid vaccines are described in Burger et al. (1991, J. Gen. Virol. 72:359–367), and are well-known in the art. See also Sambrook et al., 1989, *Molecular Cloning: A Laboratory Manual*, Cold Spring Harbor Laboratory Press, New York; Ausubel et al., 1997, *Current Protocols in Molecular Biology*, Green & Wiley, New York.

Further, cells expressing the HIV-1Env protein of choice may also be used to generate an immune response to an HIV-1 chemokine receptor binding site.

The immune response to the Env immunogen is measured by standard immunological techniques such as ELISA or Western blotting and other such techniques well-known in the art or to be developed in the future. A variety of immunoassay formats may be used to select antibodies specifically immunoreactive with a particular protein. See, e.g., Harlow and Lane (1988, Antibodies, A Laboratory Manual, Cold Spring Harbor Publications, New York) for a description of immunoassay formats and conditions that can be used to determine specific immunoreactivity.

The CD4-independent HIV-1 Env protein of the invention may be formulated in a pharmaceutical composition which is suitable for administration of the protein to a human or veterinary patient. It will be appreciated that the precise formulation and dosage amounts will vary depending upon any number of factors, including, but not limited to, the type and severity of the disease to be treated, the route of administration, the age and overall health of the individual, the nature of the Env protein, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (1985, Genaro, ed., Mack Publishing Co., Easton, Pa.).

The amount of the CD4-independent Env administered, whether it is administered as protein or as nucleic acid or as a cell expressing HIV env, is sufficient to elicit an immune response to an HIV-1 chemokine receptor binding site. The pharmaceutical compositions useful for practicing the invention may be administered to deliver a dose of between about 1 ng/kg and about 100 mg/kg of patient body weight. Suitable amounts of the CD4-independent Env protein for administration include doses which are high enough to have the desired effect without concomitant adverse effects. When the CD4-independent Env is a protein or peptide, a preferred dosage range is from about 10 to about 1000 $\mu$g of protein or peptide per kg of patient body weight. When the CD4-independent Env is administered in the form of DNA encoding the same contained within a recombinant virus vector, a dosage of between about $10^2$ and about $10^{11}$ plaque forming units of virus per kg of patient body weight may be used. When naked DNA encoding the CD4-independent Env is to be administered as the pharmaceutical composition, a dosage of between about 10 $\mu$g to about several mg of DNA per kg of patient body weight may be used.

In the practice of the methods of the invention, a composition containing a CD4-independent Env protein is administered to a patient in a sufficient amount to treat, prevent, or alleviate a HIV-1 infection in the individual.

One skilled in the art would appreciate, based on the disclosure provided herein, that the Env protein/nucleic acid encoding Env may be administered to a patient to prevent HIV infection by interfering with virus binding to the appropriate chemokine receptor using the virus' chemokine receptor binding site and, thereby preventing infection. Further, the Env protein/nucleic acid encoding env may also treat or alleviate the condition in a previously infected individual by augmenting the immune response in the person that could, in turn, be beneficial as an adjunct to antiretroviral pharmacologic therapy. That is, the immunogen may boost the immune response to the virus chemokine receptor binding site thereby generating antibodies which block the requisite interactions between the virus chemokine receptor binding site and the target cell chemokine receptor.

The frequency of administration of a CD4-independent Env protein to a patient will also vary depending on several factors including, but not limited to, the type and severity of the viral infection to be treated, the route of administration, the age and overall health of the individual, the nature of the Env protein, etc. It is contemplated that the frequency of administration of the Env protein to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate Env protein, or nucleic acid encoding same, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate Env protein or nucleic acid encoding it to a patient according to the methods of the invention.

Preferably, the composition of the invention is administered to the human by a parenteral or intravenous route.

An Env protein and/or a nucleic acid encoding Env, may be administered in conjunction with other compounds which are used to treat HIV infection. Such compounds include, but are not limited to, protease inhibitors, reverse transcriptases inhibitors (nucleoside and non-nucleoside analogs), AZT, interferons, interleukin-2, other cytokines, and the like. The choice of which additional compound to administer will vary depending upon any number of the same types of factors that govern the selection of dosage and administration frequency of the Env protein or nucleic acid encoding same. Selection of these types of compounds for use in conjunction with an Env protein for practice of the method of the invention is well within the skill of those in the art.

The invention also includes a vaccine comprising an immunogenic dose of a CD4-independent HIV-1 Env protein. As discussed previously elsewhere herein, generation of an immune response to the virus chemokine receptor binding site should block interaction of this virus site to the host chemokine receptor ligand thereby interfering with and/or inhibiting the requisite virus/host cell interaction needed for HIV infection.

In addition, the invention includes a method of identifying a compound which affects exposure of a gp120 protein chemokine receptor binding site. The method comprises contacting a cell with the compound and comparing the amount of labeled gp120 specifically bound to the cell with the amount of labeled chemokine bound to an otherwise identical cell not contacted with the compound. In one embodiment, the gp120 of interest was $^{125}$I-labeled and bound to cells expressing various chemokine receptors in the presence or absence of soluble CD4. However, the present invention should not be construed to be limited to radioiodination or to any particular gp120 or to expression of only these chemokine receptors. Rather, the invention should be construed to encompass a variety of protein labels such that binding of the gp120 of interest may be quantitated. Such methods are well-known in the art and include, but are not limited to, biotinylation, and $^{35}$S-cys and $^{35}$S-met.

The invention also includes a method of identifying a small-molecule which inhibits binding of a chemokine receptor by an HIV-1 gp120 using its chemokine receptor binding site. The method comprises contacting a cell with a small-molecule prior to or contemporaneous with contacting the cell with labeled gp120 with or without preincubation of the gp120 with soluble CD4. Then, the amount of label bound to the cell is measured thereby detecting the amount of labeled gp120 bound to the cell. The amount of bound gp120 bound to a cell contacted with the small-molecule is compared to the amount of gp120 bound to a cell not contacted with the small-molecule. If a lower amount of gp120 is bound to the cell contacted with the small molecule compared to the amount of gp120 bound to the cell which was not contacted with the small-molecule, this is an indication that contacting the cell with the small-molecule inhibits binding of HIV-1 gp120 to a chemokine receptor using its chemokine receptor binding site.

One skilled in the art would appreciate, based on the disclosure provided herein, that such small-molecules are useful therapeutics inhibiting HIV-1 infection of cells in that such small-molecules would inhibit the requisite HIV-1 gp120/chemokine receptor interactions necessary for virus infection of the target cell. Further, the prior art teaches that antibodies and chemokines which specifically bind to chemokine receptors and which block gp120 binding to the chemokine receptor often also block HIV infection (Lee et al., 1999, J. Biol. Chem., in press; Olson et al., 1999, J. Virol., in press; Wu et al., 1997, J. Exp. Med.). Thus, the small-molecule inhibitors of gp120 binding to the chemokine receptor identified using the methods of the invention are useful inhibitors of HIV infection.

Further, one skilled in the art, based upon the disclosure provided herein, would appreciate that a small-molecule inhibitor of gp120 binding using its chemokine receptor binding site to a chemokine receptor identified using the methods of the invention is a useful inhibitor of a chemokine binding to and activation of its receptor. That is, the small-molecule inhibitor may be useful for inhibiting the natural function of chemokine receptors unrelated to the role of the chemokine receptors in HIV infection. Thus, a small-molecule inhibitor identified herein is a useful therapeutic having potential uses for, among other things, immune system treatments, inflammation, and development in any non-HIV infected human.

The invention includes a method of inhibiting HIV-1 gp120 binding, using its chemokine receptor binding site, to a chemokine receptor. The method comprises contacting a the gp120 with a small-molecule which inhibits binding of gp120 to a chemokine receptor where such binding is mediated by the chemokine receptor binding site of the virus gp120 protein. The small-molecule is identified as disclosed previously elsewhere herein. Contacting the gp120 with the small-molecule binding inhibitor inhibits binding of the gp120 with the cell chemokine receptor.

The invention also includes a method of inhibiting HIV-1 infection of a cell. The method comprises contacting a cell with a small-molecule identified as described previously elsewhere herein. The small-molecule so identified inhibits the binding an HIV-1 gp120 to a cell chemokine receptor mediated by the virus gp120's chemokine receptor binding site. The small-molecule, by interfering with the requisite gp120/chemokine receptor interaction(s), thereby inhibits HIV-1 infection of the cell. Indeed, it has been demonstrated previously (Lee et al., 1999, J. Biol. Chem., in press; Olson et al., 1999, J. Virol., in press; Wu et al., 1997, J. Exp. Med.) antibodies and chemokines that block gp120 binding to the chemokine receptor often also block HIV infection. Thus, the invention includes a method of inhibiting HIV-1 infection by interfering with the receptor/ligand interactions required for HIV-1 infection of a target cell using a small-molecule inhibitor of gp120 binding to the cell chemokine receptor using the gp120 chemokine receptor binding site.

The invention also includes a composition comprising a CD4-independent HIV-1 Env and at least one compound used to treat HIV infection in a pharmaceutically suitable carrier. As described elsewhere herein, the HIV-1 Env may be a HIV-1 Env polypeptide, a nucleic acid encoding HIV-1 Env, and/or a cell expressing HIV-1 env. Further, as disclosed previously elsewhere herein, the invention should be construed to encompass compounds used to treat HIV infection such as, for example but not limited to, protease inhibitors, reverse transcriptase inhibitor, reverse transcriptase inhibitors (including both nucleoside and non-nucleoside analogs), interferons, AZT, interleukin-2, and cytokines.

The invention includes a method of treating HIV-1 infection in a human. The method comprises administering an immunogenic dose of a CD4-independent HIV-1 Env to an HIV-1 infected human. Administration of such CD4-independent HIV-1 Env induces the production of antibodies to the stably exposed chemokine receptor binding site of gp120. Thus, administration of the CD4-independent HIV-1 Env causes the production of potentially neutralizing antibodies which block the gp120/chemokine receptor interaction(s) required for HIV-1 infection of the host cell. This is suggested by the fact, disclosed elsewhere herein, that the CD4-independent gp120 is more sensitive to neutralizing antibodies than otherwise identical CD4-dependent gp120 which does not comprise a stably exposed chemokine receptor binding site. Further, antibodies that block Env-chemokine receptor interactions can neutralize HIV-1 (Wu et al., 1996, Nature 384:179–183; Trkola et al., 1996, Nature 384:184–187). Thus, increased exposure of the chemokine receptor binding site will enhance the production of antibodies to this conserved region which antibodies inhibit the requisite gp120 -chemokine receptor interactions. Therefore, immunizing a human with CD4-independent Env causes the production of antibodies to the stably exposed chemokine receptor binding site which antibodies block requisite Env-chemokine receptor interactions needed for infection,.thereby treating HIV-1 infection in the human.

One skilled in the art would appreciate, based upon the disclosure provided herein, that the immunogenic dose of a CD4-independent HIV-1 Env may be a useful therapeutic to treat and/or alleviate the HIV-1 infection in a human both before and after exposure to the HIV-1 virus. That is, the immunogenic dose may be administered prior to, during, or after infection of a human by HIV-1. Irrespective of when it is administered, the immunogen elicits a response in the human to, inter alia, the stably exposed chemokine receptor binding site of gp120 thereby inducing a response which inhibits the binding of the virus gp120 to the chemokine receptor. This inhibition is generated in both previously infected individuals as well as uninfected persons. In the individual already infected with HIV-1, the immunogen generates an immune response in addition to any immune response already present in the individual and thus mediates a reduction in the virus load in that individual. Thus, the CD4-independent HIV-1 Env is useful as a therapeutic vaccine in a human already infected by HIV-1 virus.

As disclosed previously elsewhere herein, one skilled in the art would appreciate, based on the disclosure provided herein, that the immunogenic dose of a CD4-independent HIV-1 Env may be administered as a protein, a nucleic acid (comprising a vector or as naked DNA), and/or a cell expressing a nucleic acid encoding a CD4-independent env.

In another aspect, the method of treating HIV-1 infection in a human comprises further administering a compound used to treat HIV infection. As disclosed previously elsewhere herein, such compounds include, but are not limited to, a protease inhibitors, a reverse transcriptase inhibitor, a reverse transcriptase inhibitor (including both nucleoside and non-nucleoside analogs), an interferon, AZT, interleukin-2, and a cytokine. The compound may be administered before, during, or after the administration of the immunogenic dose of a CD4-independent HIV-1 Env.

One skilled in the art would appreciate, based upon the disclosure provided herein, that the timing of the compound relative to the immunogenic dose of a CD4-independent HIV-1 Env would depend upon the immunization regimen regarding the HIV-1 Env and the particular compound(s) administered with the Env immunogen, as well as the health and age of the patient and the severity and stage of the disease process.

The HIV-1 Env immunogen(s) and/or compounds which are identified using any of the methods described herein may be formulated and administered to a mammal for treatment and/or prevention of HIV infection as now described.

The invention encompasses the preparation and use of pharmaceutical compositions comprising a compound useful for treatment of HIV infection as an active ingredient. Such a pharmaceutical composition may consist of the active ingredient alone, as a combination of at least one active ingredient (e.g., an immunogenic dose of a CD4-independent HIV-1 Env and a compound used to treat HIV infection such as interleukin-2) in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifing agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Typically dosages of the compound of the invention which may be administered to an animal, preferably a human, range in amount from 1 $\mu$g to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The compound used to treat HIV infection may be co-administered with the immunogenic dose of CD4-independent HIV-1 Env. Alternatively, the compound(s) may be administered an hour, a day, a week, a month, or even more, in advance of the immunogenic dose(s) of HIV-1 Env, or any permutation thereof. Further, the compound(s) may be administered an hour, a day, a week, or even more, after the immunogenic dose(s) of HIV-1 Env, or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and HIV-1 Env, and the like.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a HIV-1 infection means reducing the severity of the symptoms of the disease or disorder.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988, In: Antibodies:

A Laboratory Manual, Cold Spring Harbor, New York; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By "biological activity," as the term is used herein, is meant that the protein has the ability to interact with its associated protein(s) and effectuate its normal function(s) within the cell and/or with respect to HFV-1 infection. In one embodiment, the 8x gp120 retains its biological activity in that the protein does not require interaction with CD4 in order to bind to CXCR4 chemokine receptor protein, and to mediate fusion of the virus envelope with the host cell membrane. Further, biological activity as it refers to any form or fragment of Env, means that the polypeptide has the ability to bind to a chemokine receptor protein without the requirement that it also bind to CD4.

By "chemokine receptor binding site," as the term is used herein, is meant the portion of the viral gp120 which specifically binds the human chemokine receptor protein such as, but not limited to, CXCR4 or CCR5. Thus, a CXCR4 chemokine receptor binding site means a portion of the HIV-1 gp120 molecule which specifically binds to CXCR4 chemokine receptor but which does not substantially bind to another chemokine receptor such as CCR5. Similarly, a CCR5 chemokine receptor binding site means a portion of the HIV-1 gp120 molecule which specifically binds to CCR5 but which does not significantly bind to any other molecule including another chemokine receptor such as CXCR4 and the like.

By the term "CD4-independence," as the term is used herein, is meant that the HIV-1 strain is capable of infecting cells which do not express the CD4 protein and/or its gp120 can bind to a coreceptor in the absence of CD4-induced conformational change(s). However, the CD4-independent HIV-1 may also infect cells which express CD4 and an appropriate chemokine receptor, although this is not required.

By the term "chimera," as used herein, is meant a nucleic acid encoding env comprising a portion of the 8x nucleic acid encoding at least a portion of env covalently linked to at least one nucleic acid encoding a portion of an env from a different HIV-1 strain.

By the term "Env clone," as that term is used herein, is meant an env nucleic acid encoding an Env protein, gp160, comprising gp120 and gp41. A full-length Env clone encodes a complete Env protein, gp160, while a partial clone includes fragment(s) of a full-length clone that may be used to construct smaller portions of the 8x Env that may comprise mutations that are specific for 8x.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The use of the terms "nucleic acid encoding" or "nucleic acid coding" should be construed to include the RNA or DNA sequence which encodes the desired protein and any necessary 5' or 3' untranslated regions accompanying the actual coding sequence.

By the terms "encoding" and "coding," as these terms are used herein, is meant that the nucleotide sequence of a nucleic acid is capable of specifying a particular polypeptide of interest. That is, the nucleic acid may be transcribed and/or translated to produce the polypeptide. Thus, for example, a nucleic acid encoding HIV-1 Env is capable of being transcribed and/or translated to produce an HIV-1 envelope protein.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about sixty contiguous amino acids in length.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

Further, algorithms may be used to calculate the percent homology between two nucleic acids or two proteins of interest and these are well-known in the art.

By the term "immunogenic dose," as the term is used herein, is meant an amount of protein, whether it is administered as protein or as nucleic acid, which generates a detectable humoral and/or cellular immune response to the protein compared to the immune response of an otherwise identical mammal to which the protein is not administered. In one aspect, the dose is administered as Env protein or a fragment thereof. In another aspect, the dose is administered as a nucleic acid.

By the term "isolated nucleic acid," as used herein, is meant a nucleic acid sequence, or a fragment thereof, which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequences.

By the terms "isolated peptide," "isolated polypeptide," or "isolated protein," as used herein, is meant a peptide or protein which has been substantially separated from the components, e.g., DNA, RNA, other proteins and peptides, carbohydrates and lipids, which naturally accompany the protein or peptide in the cell. The terms isolated peptide and protein may be construed to include a peptide or protein which is expressed and/or secreted from a cell comprising an isolated nucleic acid.

"Mutants," "derivatives," and "variants" of the peptides of the invention (or of the DNA encoding the same) are peptides which may be altered in one or more amino acids (or in one or more base pairs) such that the peptide (or DNA) is not identical to the sequences recited herein, but has the same property as the peptides disclosed herein, in that the peptide has the property of binding to a chemokine receptor protein in a CD4-independent manner.

As used herein, the term "pharmaceutically-acceptable carrier" means a chemical composition with which an appropriate Env protein, may be combined and which, following the combination, can be used to administer the protein to a patient.

By the term "specifically binds," as used herein, is meant a chemokine receptor binding site which recognizes and binds, for example, CXCR4 polypeptide, but does not substantially recognize or bind other molecules in a sample. Similarly, a chemokine receptor binding site "specifically binds CXCR4" if the binding site recognizes and binds CXCR4 in a sample but does not substantially recognize or bind to other molecules, e.g., CCR5, in a sample. Similarly, a chemokine receptor binding site may specifically bind CCR5 and, thus, would not bind other molecules such as CXCR4.

A swarm refers to an uncloned stock of HIV from infected cells. Such stocks are known to contain many genetically distinct variants of a founder or a parental virus, hence the term "swarm."

The term "stably exposed chemokine receptor binding site," as used herein, means that the gp120 chemokine receptor binding site is available to bind to the chemokine receptor protein without the need for gp120 interaction with CD4 which typically, is a prerequisite to gp120 binding of the chemokine receptor protein. As demonstrated by the data disclosed herein, the chemokine receptor binding site of gp120 can exist in a stable, exposed configuration which is more sensitive to antibody neutralization than the otherwise identical CD4-dependent gp120 prior to binding of CD4. The stably exposed form of the chemokine binding site can exist in solution for a period of at least about three months and/or indefinitely.

As used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest. Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state.

As used herein, to "treat" means reducing the frequency with which symptoms of the HIV-1 infection are experienced by a patient.

By "triggered," as the term is used herein, it is meant that the HIV-1 Env protein does not require binding to CD4 before gp120 can bind to a chemokine receptor protein such as CXCR4 or CCR5. Preferably, a triggered Env comprises a gp120 that is in a conformation that can bind chemokine receptors in the absence of binding to CD4.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the HIV-1 Env protein or nucleic acid encoding the HIV-1 env, to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

By the term "vaccine," as the term is used herein, is meant a compound which when administered to a human or veterinary patient, induces a detectable immune response, humoral and/or cellular, to HIV-1 or a component(s) thereof.

EXAMPLE 1

Determinants of CD4-independence for an HIV-1 Map Outside Regions Required for Coreceptor Specificity The experiments presented in this example may be summarized as follows.

Although infection by HIV typically requires an interaction between the viral envelope glycoprotein (Env), CD4, and a chemokine receptor, CD4-independent isolates of HIV and SIV have been discovered herein. The present invention discloses the derivation of a variant of HIV-1/IIIB, termed HIV-1/IIIBx, which exhibits the ability to utilize CXCR4 in the absence of CD4. This virus infected CD4-negative T and B cells and fused with murine 3T3 cells expressing human CXCR4 alone.

A functional HIV-1/IIIBx env clone exhibited several mutations, including the striking loss of 5 glycosylation sites. The data disclosed herein demonstrate the construction of chimeras with CD4-dependent envs. The data disclose that the determinants for CD4-independence map outside the V1/V2 and V3 hypervariable loops, which determine chemokine receptor specificity, and, at least in part, within an area on the gp120 core that has been implicated in forming a conserved chemokine receptor binding site. Further, the data disclosed herein demonstrate that when the V3 loop of a CCR5-tropic Env was substituted into the HIV-1/IIIBx Env, the resulting chimera utilized CCR5 but remained CD4-independent. Thus, the data disclosed demonstrate, for the first time, that Env determinants for chemokine receptor specificity are distinct from those that mediate use of that receptor for cell fusion. These findings provide evidence that mutations in HIV-1/IIIBx expose a conserved chemokine receptor binding site that can interact with either CXCR4 or CCR5 in the absence of CD4 and may have important implications for designing Envs with exposed chemokine receptor binding sites for vaccine development.

The data presented herein disclose the derivation and molecular characterization of a variant of HIV-1/IIIB, termed HIV-1/IIIBx, which acquired the ability to utilize CXCR4 in the absence of CD4. A functional HIV-1/IIIBx env clone (8x) was used to construct chimeras with a closely related but CD4-dependent env, and the determinants for CD4 independence were shown to map in part, to the conserved chemokine receptor binding site and outside the variable loops. Remarkably, when 8x contained the V3 loop of a CCR5-tropic Env, it utilized CCR5 but maintained CD4 independence. These findings provide evidence that CD4 binding likely exposes a domain on the gp120 core that can interact with genetically divergent chemokine receptors. This work may have important implications in designing HIV-1 Env proteins with exposed chemokine receptor contact sites that could exhibit novel biochemical and immunogenic properties.

The Materials and Methods used in the experiments presented in this example are now described.

Cells, Viruses and Infectivity Assays.

Hut-78 and SupT1 are immortalized CD4+ T cell lines. BC7 is a CD4-negative line derived from SupT1 (Endres et al., 1996, Cell 87:745–756). Uncloned HIV-1/IIIB was obtained in chronically infected Hut-78 cells as described in Popovic et al. (1984, Science 224:497–500). Supernatant virus from this infected Hut-78 cell culture was serially passaged onto SupT1 cells from which HIV-1/IIIBx was isolated by subsequent passage onto BC7. The IIIB/Sup virus was derived from early passage HIV-1/IIIB in SupT1. NIH-3T3 cells, untransfected and stably transfected with human CXCR4, were described in (Deng et al., 1996, Nature 381:661–666). Reverse transcriptase (RT) assays were performed on culture supernatants as described in Endres et al. (1997, Science 278:1462–1464). For neutralization assays, BC7 cells were preincubated with varying concentrations of anti-CXCR4 MAb, or 12G5 (Endres et al., 1997, supra), for 30 minutes at 37° C., the cells were then inoculated with HIV-1/IIIBx (10 $TCID_{50}$) and the cells were monitored for RT activity.

PCR, Cloning, Virus Production and Chimera Construction.

Full-length env coding regions were amplified by PCR from genomic DNA of chronically infected cells using the sense primer 5'-CGCAACCTATACCAATAGTAGCAA-3' [SEQ ID NO:1] and the antisense primer 5'-CAGTAAGCCATCCAATCACACTAC-3' [SEQ ID NO:2] in a BioCycler (Ericomp, San Diego, Calif.). The PCR product was TA-cloned into pCDNA3.1 (Invitrogen, San Diego, Calif.) and tested in a reporter gene fusion assay. Functional clones of HIV-1/IIIBx (8x) and IIIB/Sup (S10) were sequenced using an automated sequencer. Clones were also subcloned into pSP73 (Promega Corp., Madison, Wis.) that contained the HXBc2 env using Asp718 and BamH1 (Hoffman et al., 1998, Proc. Natl. Acad. Sci. U.S.A. 95:11360–11365).

Functional env clones were sub-cloned into the 3' hemigenome of pNL4-3 (from the EcoRI site) using unique NdeI and BamHI restriction sites in env, which encompass the mutations in HIV-1/IIIBx and IIIB/Sup. Virus was generated by digesting 20 μg each of the 5' pNL4-3 Δvpr hemigenome (to the EcoRI site) (Gibbs et al., 1994, AIDS Res. Hum. Retroviruses. 10:343–350) and the various 3' hemigenome constructs with EcoRI, phenol extracting, and coprecipitating before transfection into BC7 and SupT1 by electroporation. Cells were monitored for syncytia formation and supernatant virus harvested to generate virus stocks. HIV-1/IIIB virus stocks were frozen at −70° C. in 1 ml aliquots. HIV-1/IIIBx and 8x virus stocks were frozen at −140° C. in 5% sucrose to preserve infectivity. Chimeras between 8x and S10 or HXBc2 (Hoffman et al., 1998, Proc. Natl. Acad. Sci. U.S.A. 95:11360–11365) were constructed using a BsaBI site (nt 7673) to isolate changes in SU (i.e., the gp120 portion of Env which is the surface portion of Env) from TM (i.e., the gp41 portion of Env which is the transmembrane portion of Env) and DraIII (nt 6714), StuI (nt 6948), and Bsu36I (nt 7430) to isolate V1–V2, V3, and V4/C4 regions, respectively. Clones containing the V3 loop of an R5 virus were constructed by subcloning the Asp718-BamHI fragment from a proviral clone of HXB with the V3 loop of BaL (Hwang et al., 1991, Science 253:71–74) into pSP73-HXBc2 (Hoffman et al., 1998, Proc. Natl. Acad. Sci. U.S.A. 95:11360–11365). A version of 8x containing the V3-loop of BaL was made in a similar fashion, by inserting the StuI-Bsu36I fragment of this provirus into pSP73-8x.

Cell-cell Fusion Assay.

The ability of env genes to mediate cell-cell fusion was evaluated using a luciferase-based gene reporter assay (Rucker et al., 1997, Methods Enzymol. 288:118–133). Briefly, quail QT6 cells were co-transfected with plasmids containing HIV envs by $CaPO_4$ and infected with a vaccinia virus expressing T7 RNA polymerase (Alexander et al., 1992, 1992, J. Virol. 66:2934–2942). These cells were mixed with quail QT6 cells transiently expressing human CXCR4 or CCR5 with or without human CD4 and the luciferase gene under the control of the T7 promoter. Fusion was quantified by lysing the cells 7–8 hours after combining the cells and measuring luciferase expression with a luminometer.

Reverse Transcriptase Assays.

The productive infection of cells was documented by detection of the reverse transcriptase (RT) activity in the culture supernatant as previously described (Hoxie et al., 1985, Science 229:1400–1402). Briefly, virus from 1 ml of clarified culture supernatant was pelleted at 100,000×g for 30 minutes at 4° C. and the virus was solubilized in 100 µl solubilizing buffer (0.15 M Tris pH 8, 0.4 M NaCl, 0.25% Triton X-100, 10% glycerol, 0.5 mM D.T.). Duplicate 20 µl aliquots were mixed with 85 µl RT cocktail (67.5 mM Tris pH 7.5, 1.3 mM D.T., 1 mM ATP, 13.5 mM $MgCl_2$ containing 0.05 units poly r(A) and 12.5 µCi $^3$H-dTTP) and incubated for 1 hour at 37° C. The tubes were placed on ice, 225 µg tRNA was added to each tube, and RNA was precipitated with cold 10% TCA. Precipitated RNA was captured on a glass fiber filter, and the RNA was washed with TCA and EtOH. The filters were dried and the radioactivity present on each filter (in counts per minute, cpm) was determined in a scintillation counter (LKB/Wallac, Turku, Finland).

Mutagenesis.

Point mutations were engineered into Env constructs in pSP73 using the Quickchange™ Site Directed Mutagenesis Kit (Stratagene, La Jolla, Calif.) according to the manufacturer's specifications. The following primer pairs produced the D368R mutation that ablated CD4 binding: D368R-forward, 5'CCTCAGGAGGGGACCCAGAAATTGTAACGC-3' (SEQ ID NO:5); D368R-reverse, 5'GCGTTACAATTTCTGGGTCCCCTCCTGAGG-3' (SEQ ID NO:6).

Reciprocal exchange of residues at position 431 in 8x and S10 was accomplished using two sets of oligonucleotides:

8x-G431E-forward 5'-GGCAGGAAGTAGAAAAAGCAATGTATGCCCC-3' (SEQ ID NO:7) and 8X-G431E-reverse 5'GGGGCATACATTGCTTTTTCTACTTCCTGCC-3' (SEQ ID NO:8); and S10-E431G-forward 5'-GGCAGGAAGTAGGAAAAGCAATGTATGCCCC-3' (SEQ ID NO:9) and S10-E431G-reverse 5'-GGGGCATACATTGCTTTTCCTACTTCCTGCC-3' (SEQ ID NO:10).

Western Blot.

Virus isolated from the supernatant of an infected cell culture was pelleted at 100,000×g for 90 minutes at 4° C., and the virus pellet resuspended in lysis buffer (20 mM Tris pH 8.0, 120 mM NaCl, 0.2% sodium deoxycholate, 0.5% NP-40, 0.2 mM EGTA, 0.2 mM NaF, 1 μM pepstatin, 5 μg/ml leupeptin, 5 μg/ml aprotinin) on ice. Equal volumes of lysate and 2×sample buffer (50 mM Tris, pH 6.8, 2% SDS, 30% glycerol, 10% β-mercaptoethanol, 0.2% pyronine Y) were boiled for 7 minutes, chilled on ice for 7 minutes, and the samples were then run on a 12% SDS-PAGE gel.

The proteins were transferred from the gel to nitrocellulose (BioRad Laboratories, Richmond, Calif.) using a Multiphor II semi-dry electrotransfer apparatus (Pharmacia-LKB Biotechnology Inc., Piscataway, N.J.). The presence of HIV-1 transmembrane proteins was detected on the blot using the D12 mouse monoclonal antibody as described in Earl et al. (1997, J. Virol. 71:2674–2684), followed by biotinylated sheep anti-mouse IG (heavy and light chains) (Jackson ImmunoResearch Laboratories, West Grove, Pa.), streptavidin-conjugated to horse radish peroxidase (streptavidin-HRP, Amersham, Arlington Heights, Ill.) and chemiluminescence substrate (Pierce Chemical Co., Rockford, Ill.).

The Results of the experiments presented in this example are now described.

Derivation of a CD4-independent Variant of HIV-1/IIIB.

A CD4-independent variant of HIV-1/IIIB was derived by serial passage of an uncloned stock of HIV-1/IIIB in SupT1 and then inoculating BC7, a CD4-negative line of SupT1 (Endres et al., 1996, Cell 87:745–756). In one experiment, approximately 5% of BC7 cells were positive for viral $p24^{gag}$ by immunofluorescence assay (IFA). Virus from this culture was passaged twice onto uninfected BC7 cells and a chronically infected line was established. Virus from this line, termed HIV-1/IIIBx, was compared to an earlier passage of HIV-1/IIIB in SupT1 cells, designated IIIB/SupT1. As shown in FIG. 1A, only HIV-1/IIIBx could infect BC7 while both viruses were able to infect SupT1. HIV-1/IIIBx was also able to infect Raji cells, a CD4-negative B lymphoblastoid cell line. Infection of BC7 could be completely inhibited by the anti-CXCR4 MAb, 12G5 (FIG. 1B), indicating that this infection was likely mediated by CXCR4. Moreover, HIV-1/IIIBx-infected BC7 cells induced syncytia when cocultured with murine 3T3 fibroblasts that stably expressed human CXCR4 while no fusion was induced on untransfected 3T3 cells (FIG. 1C). In addition, no fusion was observed when HIV-1/IIIB-infected HUT-78 cells were cocultured with the CXCR4-expressing 3T3 cells. Together, these data indicate that the HIV-1/IIIBx variant can utilize CXCR4 as a primary receptor in the absence of CD4 on T and B lymphoid cell lines and murine fibroblasts.

Cloning and Characterization of a Functional HIV-1/IIIBx env.

A full length env clone of HIV-1/IIIBx (designated 8x) (SEQ ID NO:4) was amplified by PCR from infected BC7 cells, cloned into pSP73, and compared to a prototypic CD4-dependent IIIB clone (HXBc2) in a cell fusion assay. Both 8x and HXBc2 were able to mediate fusion on quail QT6 cells expressing both CD4 and CXCR4, but only 8x could fuse with cells that expressed CXCR4 alone (FIG. 2). Of note, 8x fusion was enhanced when CD4 and CXCR4 were co-expressed, indicating that the 8x Env was likely still able to interact with CD4. Additionally, the 8x env cloned into the pNL4-3 provirus generated a replication competent virus that infected SupT1 as well as BC7 cells (FIG. 3A), providing further proof that the 8x Env was able to utilize CXCR4 in the absence of CD4, and that the 8x clone was representative of the uncloned parental IIIBx virus.

The CD4-independence of the 8x was further evaluated by introducing an Asp to Arg substitution at gp120 amino acid position 368. This Asp is highly conserved among all HIV-1 isolates and is a critical determinant for CD4 binding by forming a salt bridge with Arg-59 in the CDR2 loop of CD4 (Kwong et al., 1998, Nature 393:648–659). Mutations at this position have been shown to ablate CD4-binding (Olshevsky et al., 1990, J. Virol. 64:5701–5705). As shown in FIG. 2, although a D368R (i.e., Asp to Arg at amino acid 368) mutation abrogated fusion by HXBc2 on cells that coexpressed CD4 and CXCR4, this mutation did not affect 8x-mediated fusion on target cells expressing only CXCR4. Unlike the 8x clone, fusion of 8x-D368R was not enhanced when CD4 was co-expressed with CXCR4, confirming that the 8x-D368R Env was unable to interact with CD4. Thus, the 8x Env was not only able utilize CXCR4 in the absence of CD4, but could tolerate a mutation that destroyed the CD4 binding site on gp120.

Sequence Analysis of env Clones.

Sequences of 8x (SEQ ID NO:3) and S10 (SEQ ID NO:12) were compared to the published sequence of HXBc2 (SEQ ID NO:11) (FIG. 4). While the number of mutations in 8x is large (16 in gp120 and 7 in TM), 6 of the mutations in gp120 and 2 in TM have been observed in other env clones derived from HIV-1/IIIB and, thus, are likely not involved in the CD4-independent phenotype. In gp120, 8 of the 11 unique mutations were in the hypervariable loops, V1/V2 (S143G, I165K, G167S, Q170K, and T188P), V3 (R298K, Q310H, and I320V), and V4 (N386K). Three mutations were in the gp120 core (D62E, N339S, I423V). Interestingly, 5 mutations in the gp120 resulted in the loss of potential N-linked glycosylation sites, and 4 of these (S143G, T188P, N339S, and N386K) were unique to 8x. The 4 8x-specific mutations in the external domain of TM were located within the two regions that form coiled coils (T536A, L544S, N6511 and K655M). Remarkably, 8x also contained a single nucleotide deletion in the TM membrane-spanning domain that introduced a frame-shift at position 706 generating a divergent cytoplasmic tail of only 30 amino acids. This feature is surprising since HIV-1 viruses with truncated cytoplasmic tails typically have been attenuated or non-infectious (Shimizu et al., 1992, Virology 189:534–546; Dubay et al., 1992, J. Virol. 66:6616–6625; Chen et al., 1996, Virology 226:260–268). Nonetheless, as noted above, the 8x Env was able to generate a replication competent virus that could infect SupT1 as well as BC7 cells (FIG. 3A). Moreover, western blots of viral lysates from uncloned HIV-1/IIIBx as well as from NL4–3 containing the 8x env demonstrated a TM of approximately 35 kD compared to 41 kD for parental HIV-1/IIIB (FIG. 3B).

Mapping CD4-independence Using Chimeric Env Proteins.

To identify determinants of CD4-independence, a set of reciprocal chimeras was generated between 8x and HXBc2. Unique restriction sites were chosen to isolate mutations in gp120 from those in TM and to define the effects of mutations in the V1/N2, V3, and the V4/C4 subdomains (FIG. 5). Chimeras were cloned into pSP73 and were analyzed in fusion assays as described herein on target cells expressing CXCR4 alone or with CD4. The results for each chimera are expressed as the percentage of fusion activity of the HXBc2 Env fusion activity on target cells that expressed both CXCR4 and CD4. All chimeras were functional when CXCR4 and CD4 were coexpressed on the target cells, although considerable quantitative differences were detected with fusion activities ranging from about 50% to about 500% that of HXBc2 (FIG. 6). Reciprocal chimeras that exchanged the entire gp120 and TM were CD4-dependent, although an assessment of the 8x gp120 with an HXBc2 TM [8x (gp120)] was somewhat limited due to the poor overall fusion activity of this Env. Of note, chimeras that contained the 8x TM were more fusogenic than HXBc2 or chimeras that contained an HXBc2 TM, suggesting that determinants in the 8x ectodomain or the prematurely truncated cytoplasmic tail were contributing to the increased fusogenicity of these clones. Nonetheless, these finding suggested that determinants for CD4-independence were not entirely restricted to gp120 or TM.

Among chimeras that introduced gp120subdomains of HXBc2 into an 8x background, replacement of V1/V2 and V3 loops either individually or in combination failed to eliminate CD4-independence (FIG. 6; see chimeras HX(V1/V2), HX(V3), HX(V1–V3)). This finding was of interest given the importance of these loops as determinants of chemokine receptor specificity (Cho et al., 1998, J. Virol. 72:2509–2515; Choe et al., 1996, Cell 85:1135–1148; Cocchi et al., 1996, Nature Med. 2:1244–1247; Hoffman et al., 1998, Proc. Natl. Acad. Sci. USA 95:11360–11365; Ross and Cullen, 1998, Proc. Natl. Acad. Sci. USA 95:7682–7686; Speck et al., 1997, J. Virol. 71:7136–7139). For these chimeras, fusion activity relative to 8x was reduced (80%) on both CD4-negative and -positive cells, although CD4-dependent fusion was still greater than that seen with HXBc2. In contrast, fusion activity of HX(v4/C4), which contained the HXBc2 V4/C4, was reduced on CD4 negative cells but was unchanged on CD4+ cells. Interestingly, when both the V3 and V4/C4 domains of 8x were replaced with those of HXBc2 [HX(V3-C4)], CD4-independent fusion was completely abrogated, while fusion in the presence of CD4 was unaffected.

For chimeras in which domains of 8x were placed on an HXBc2 background, no single region of gp120 was able to confer CD4-independence to HXBc2, consistent with evidence noted above that determinants in both gp120 and TM are required (FIG. 6). However, an HXBc2 chimera that contained both the V4/C4 and TM domains from 8x [8x (V4-TM)] was highly competent for both CD4-dependent and independent fusion. Collectively these findings with 8x- and HXBc2-based chimeras indicate that determinants in the 8x gp120 V3 and, particularly, the V4/C4 domain contribute to the CD4-independent phenotype of 8x, but only when associated with the 8x TM.

Evaluation of a CD4-dependent Clone from IIIBx-infected Cells.

A CD4-dependent Env was also derived from IIIBx-infected SupT1 cells. This clone, termed S10, was able to mediate fusion on QT6 cells that coexpressed CXCR4 and CD4, but was unable to fuse in the absence of CD4 (FIG. 7). Sequence analysis demonstrated that S10 shared several mutations with 8x relative to HXBc2 (8 in gp120 and 3 in gp4 1) (FIG. 4). In addition, S10 contained several unique mutations: in gp120, G431E in C4 and S461N in V5, and in TM, six additional amino acid changes in the ecto-and membrane spanning domains, including the loss of predicted N-lined glycosylation sites at positions 611 and 674 (FIG. 4). S110 also contained a 55 nt deletion in the TM cytoplasmic tail that, similar to 8x, produces a frameshift mutation and a prematurely truncated cytoplasmic tail. This deletion also disrupts the rev open reading frame by eliminating the nuclear localization signal at the N terminus and introducing a frame-shift mutation that truncates the protein before the RRE-binding site (Pollard and Malim, 1998, Annu. Rev. Microbiol. 52:491–532). Finally, S10 lacked several changes that were present in the 8x gp120 (S143G, G167S, Q310H, and I423V) and TM (N651I). Even though S10 was functional in fusion assays on CD4+/CXCR4+ target cells, this env was unable to generate infectious virus when cloned into NL4-3, likely as a result of its non-functional Rev Protein.

Because the S10 Env shared several mutations with 8x but was completely CD4-dependent, a set of chimeras between 8x and S10 were made to identify the determinants for this change. As shown in FIG. 7, chimeras that contained the 8x V3 and V4/C4 [8x(V3-C4)] or V4/C4 alone [8x (V4/C4] on an S10 background exhibited some CD4-independence while the reciprocal chimeras on an 8x background, [S10 (V3-C4)] and [S10(V4/C4)], were completely CD4-dependent. Because the S10 V4/C4 domain contained a unique G431E mutation, the possibility that this change could have a negative effect on CD4-independence was considered. Indeed, when a Gly was restored at this position in S10 (S10-E431G), this clone exhibited a limited degree of CD4-independence on CXCR4-expressing target cells. Moreover, when the G431E mutation was introduced into 8x (8x-G431E), this clone remained fusion competent but became completely CD4-dependent (FIG. 7). Thus, a charge change within the C4 domain was sufficient to abrogate CD4-independence of 8x, and these data further support the mapping data obtained using the 8x/HXBc2 chimeras described above that implicated this region as being critical to the CD4-independent phenotype.

CCR5-tropic V3 Loop Alters Chemokine Receptor Specificity but not CD4-independence.

Given the importance of the V3 loop in determining chemokine receptor specificity and the evidence that determinants for CD4 independence were located outside this domain, the extent to which tropism and CD4-independence of 8x could be dissociated was examined. An HXB2 gp120 that contained the V3 loop from the macrophage/CCR5-tropic isolate HIV-1/BaL (HXB2-V3BaL) (Hwang et al., 1991, Science 253:71–74) was used to introduce the BaL V3 loop into 8x. The resulting chimera (8x-V3BaL) was compared to 8x, HXBc2 and HXB2-V3BaL in fusion assays on target cells that expressed CXCR4 or CCR5, in the presence or absence of CD4 (FIG. 8). As the data disclosed herein demonstrate, HXBc2 and HXB2-V3BaL exhibited fusion on CXCR4- or CCR5-expressing cells, respectively, and their activity was strictly CD4-dependent. In contrast, the 8x-V3BaL chimera was both CCR5-tropic and CD4-independent. Thus, determinants for CD4-independence of 8x are functionally distinct from those that mediate chemokine receptor tropism.

The data disclosed herein demonstrate the derivation and characterization of a CD4-independent variant of HIV-1/IIIB, termed HIV-1/IIIBx, that could utilize CXCR4 in the absence of CD4. The 8x env clone of IIIBx was able to generate a replication competent, CD4-independent virus when cloned into an HIV-1 provirus and could mediate fusion on CXCR4-expressing quail cells in the absence of CD4. This clone was also fully functional when Arg was substituted for Asp at gp120 position 368, a residue previously shown to be critical to the formation of the DE4 binding site (Kwong et al., 1998, Nature 393:648–659; Olshevsky et al., 1990, J. Virol. 64:5701–5705). Sequence analysis of 8x revealed 17 mutations that have not been described in other HIV-1/IIIB proviral clones and a remarkable net loss of 5 glycosylation sites on gp120. Reciprocal chimeras between 8x and a related CD4-dependent clone, HXBc2, indicated that the determinants for CD4 independence mapped outside the hypervariable V1/V2 and V3 loops. An HXBc2 chimera that contained both the V4/C4 and TM domains of 8x was CD4-independent while chimeras that contained either domain alone were CD4-dependent. In addition, a CD4-dependent clone from the IIIBx swarm, S10, that contained a unique G431E mutation in the gp120 C4 domain became CD4-independent when this mutation was corrected. Introduction of the G431E mutation into 8x rendered this Env completely CD4-dependent, indicating that a charge change at this position was sufficient to disrupt CD4-independent but not CD4-dependent utilization of CXCR4. Collectively, these findings indicate that a chemokine receptor binding site exists on the gp120 core, and that mutations in this region can, in association with alterations in TM, render an HIV-1 Env fully functional in the absence of CD4.

The HIV-1 V3 loop has been shown to be a principal determinant for chemokine receptor specificity for CCR5 or CXCR4 following CD4 binding (Cho et al., J. Virol. 72:2509–2515; Choe et al., 1996, Cell 85:1135–1148; Cocchi et al., 1996, Nature Med. 2:1244–1247; Speck et al., 1997, J. Virol. 71:7136–7139; Trkola et al., 1998, J. Virol. 72:1876–1885; Wu et al., 1996, Nature 384:179–183). More recently, the V1/V2 region has also been shown, in the context of an appropriate V3, to mediate use of additional chemokine receptors including CCR3, CCR2b, STRL33, and APJ (Hoffman et al., 1998, Proc. Natl. Acad. Sci. USA 95:11360–11365; Ross and Cullen, 1998, Proc. Natl. Acad. Sci. USA 95:7682–7686) suggesting that cooperative interactions between V1/V2 and V3 are involved in chemokine receptor recognition. These loops are known to undergo conformational changes following CD4 binding (Jones et al., 1998, J. Biol. Chem. 273:404–409; Moore et al., 1994, J. Virol. 68:469–484; Wu et al., 1996, Nature 384:179–183; Wyatt et al., 1992, J. Virol. 66:6997–7004) that may facilitate an interaction with a particular chemokine receptor (Jones et al., 1998, J. Biol. Chem. 273:404–409; Wu et al., 1996, Nature 384:179–183; Wyatt et al., 1992, J. Virol. 66:6997–7004). However, while these findings have suggested that V3 itself may contain a chemokine receptor binding site, the marked genetic diversity of V3 loops among CCR5- or CXCR4-tropic viruses indicates either that these loops contain a common structural element or that other regions on Env also contribute to chemokine receptor utilization. Recently, mutagenesis of a CCR5-tropic HIV-1 gp120 has identified a probable CCR5 binding site on Env that is formed by a bridging sheet that connects the inner and outer domains of the gp120 core. This region is located between the bases of the V1/V2 and V3 loops and is predicted to be oriented towards the cell membrane following CD4 binding (Rizzuto et al., 1998, Science 280:1949–1953). The remarkable conservation of amino acids in this region among CCR5- and CXCR4-tropic Envs has suggested that this site could represent a generic chemokine receptor binding domain capable of interacting with multiple chemokine receptors. These findings are consistent with a model in which CD4-induces movement of the V1/V2 and V3 loops, which facilitates an initial interaction with a specific chemokine receptor and exposes this conserved binding site that is then required for fusion to occur (Rizzuto et al., 1998, Science 280:1949–1953; Wyatt and Sodroski, 1998, Science 280:1884–1888).

Because determinants for CD4-independence of the 8x clone mapped outside regions required for chemokine receptor specificity, the possibility that a different V3 might change the chemokine receptor tropism of 8x without affecting its CD4-independence was investigated. Remarkably, the data disclosed herein demonstrate that when the V3 loop from a CCR5-tropic Env (HIV-1BaL) was inserted into 8x, the resulting chimera was able to mediate CD4-independent fusion on CCR5-expressing cells. No fusion on CXCR4-expressing cells with or without CD4 was observed for this chimera. In contrast, a chimera containing the HIV-1/BaL V3 loop on an HXBc2 background utilized CCR5 but was completely CD4-dependent. These data clearly indicate that chemokine receptor specificity and the utilization of that receptor for fusion are mediated by distinct regions of gp120. Moreover, the data disclosed herein also provide direct evidence that, although specificity determinants on V3 are still required, a region on the gp120 core that is rendered functional on CD4-independent viruses is able to mediate fusion using genetically divergent chemokine receptors.

The bridging sheet on gp120 noted above is made up largely of amino acids from the C4 domain and the V1/V2 stem (Rizzuto et al., 1998, Science 280:1949–1953). This region has also been shown to contribute to the formation of gp120 epitopes that are induced by CD4 binding (Kwong et al., 1998, Nature 393:648–659; Thali et al., 1993, J. Virol. 67:3978–3988). Interestingly, the two mutations in the 8x V4/C4 domain (N386K and I423V) and a third mutation near the base of the V3 loop (R298K) map to positions that immediately flank this area (FIG. 9A). As the data disclosed herein demonstrate, an 8x chimera that included the corresponding V3 and V4/C4 domains from HXBc2 and that lacked these mutations was highly competent for fusion but was completely CD4-dependent (FIG. 6). Without wishing to be bound by theory, the remarkable proximity of R298K, N386K, and I423V to the putative chemokine receptor binding domain strongly suggests that these mutations expose this site and/or help to present it to the chemokine receptor during viral attachment. Further, data disclosed elsewhere herein (Example 2, infra) demonstrate that recombinant 8x gp120 is able to bind to CXCR4-expressing cells independently of CD4 and that CD4-induced epitopes that are partially contained within the gp120 chemokine receptor domain are stably exposed in the absence of CD4 binding. In addition, the G431E mutation in C4, which was sufficient to abrogate CD4-independence on S10 and 8x, is shown by the crystal structure of the gp120 core to be juxtaposed to residues at the base of the V1/V2 stem that contribute to the chemokine receptor binding site (FIG. 9B). Without wishing to be bound by theory, the acquisition of a negative charge at this residue could alter the orientation of the V1/V2 loops and/or affect the conformation of the chemokine receptor binding site on gp120. Regardless of the mechanism, it is apparent that mutations in or around this chemokine receptor binding site can impact positively or negatively on the ability of the 8x Env to function without CD4 and is consistent with the view that CD4 binding improves the overall efficiency and/or avidity of chemokine receptor utilization.

While the V4/C4 domain is clearly involved with CD4-independence of IIBx, it is apparent that other regions of the Env also contribute to this phenotype. A chimera that contained the 8x V4/C4 on an HXBc2 background was only CD4-independent when it also contained the 8x TM. A previous study by Reeves et al. (1996, J. Virol. 71:1453–1465) of the CD4-independent HIV-2/ROD-B demonstrated that mutations in both gp120 and in TM were the minimal requirements for this phenotype (i.e., a Leu to Phe mutation just proximal to the analogous V4 loop of HIV-1, and two mutations in the first heptad repeat of the TM ectodomain). Although the underlying mechanism for this effect is unclear, regions of the HIV-1 TM have been implicated in a number of cooperative interactions with the gp120 that could affect its binding to CD4 and/o to chemokine receptors (Cao et al., 1993, J. Virol. 67:2747–2755; Chan et al., 1997, Cell 89:263–273; Matthews et al., 1994, Immunol. Rev. 140:93–104). Of note, the gp120 chemokine receptor binding site described above is located near the predicted trimer axis of the assembled Env oligomer where interactions with TM are likely to occur (Haigwood et al., 1992, J. Med. Primatol. 21:82–90). The data obtained in recent experiments demonstrate that and HXBc2 chimera containing only the 8x V4/C4 and the 8x frameshift mutation in TM was able to mediate CD4-independent fusion to a level approximately 10% that of 8x. Whether this small but reproducible effect is due to an increase in the surface expression of Env on transfected cells (LaBranche et al., 1995, J. Virol. 69:5217–5227; Mulligan et al., 1992, J. Virol. 66:3971–3975) or whether the effect is due to structural alterations in the TM ectodomain (Ritter et al., 1993, Virology 197:255–264; Spies et al., 1994, J. Virol. 68:585–591), and/or gp120 (Cao et al., 1993, J. Virol. 67:2747–2755; Chan et al., 1997, Cell 89:263–273; Matthews et al., 1994, Immunol. Rev. 140:93–104) remains to be determined.

Further, 8x contains mutations that are predicted to eliminate 5 glycosylation sites in gp120, including N386K as noted previously elsewhere herein, which mutation lies adjacent to the putative chemokine receptor binding site. Carbohydrates have recently been implicated in modifying the immunogenicity of SIV gp120 and in masking neutralization epitopes (Reitter et al., 1998, Nature Med. 4:679–684). Without wishing to be bound by theory, it is possible that the loss of one or more glycosylation sites could also be involved in exposing the chemokine receptor binding site.

Although the data disclosed herein have implicated mutations in the IIIBx V4/C4 and TM as determinants for CD4-independence, it should be noted that mutations in different regions of gp120 have been associated with CD4-independence for other HIV-1 isolates. A CD4-independent variant of HIV-1/NDK has been described that could infect HeLa cells using CXCR4 by virtue of a combination of mutations in the C2, C3, and V3 domains (Dumonceaux et al., 1998, J. Virol. 72:512–519). Recent findings by Sodroski et al., have demonstrated that determinants for a CD4-independent, CCR5 tropic variant of HIV-1/ADA mapped to point mutations in the distal region of the V1/V2 stem. Despite these genetic differences, CD4-independent viruses could have a similar structural basis for this phenotype. In this regard, at least some of the changes in CD4-independent HIV-1/NDK and HIV-1/ADA are similar to IIIBx, being located near the gp120 bridging sheet where they could affect the presentation of this region to a chemokine receptor.

HIV has evolved strategies that enable viral replication to continue in spite of a vigorous host immune response (Wei et al., 1995, Nature 373:117–122; Perelson et al., 1996, Science 271:1582–1586). Neutralizing antibodies typically arise late in the course of infection, if at all, and are frequently directed at type-specific rather than group-specific determinants on gp120 (Wyatt and Sodroski, 1998, Science 280:1884–1888; Moore and Ho, 1995, AIDS 9:S117–S136). The deduced crystal structure of the gp120 core has suggested that the CD4 binding domain and the chemokine receptor binding site are poorly accessible and/or are concealed within the Env oligomer (Wyatt and Sodroski, 1998, Science 280:1884–1888; Rizzuto et al., 1998, Science 280:1949–1953). In contrast, the exposed surfaces of gp120 contain hypervariable domains and carbohydrates that may serve as immunologic decoys for the humoral immune response (Stamatatos and Cheng-Mayer, 1998, J. Virol. 72:7840–7845; Reitter et al., 1998, Nature Med. 4:679–684; Cao et al., 1997, J. Virol. 71:9808–9812). Approaches to expose these conserved and functionally critical domains may enable qualitatively different and perhaps more efficacious immune responses to be generated. Recent studies by LaCasse et al. (1999, Science 283:357–362), have demonstrated that a fusion-activated form of Env in which conserved neutralization epitopes on gp120 and gp41 were apparently stabilized was able to generate a potent and broadly cross-neutralizing antibody response in mice. In this regard, CD4-independent Envs that are derived or designed may provide a means to present these domains in a biologically relevant context. Data disclosed elsewhere herein demonstrate that the 8x gp120 exhibits a number of novel immunological and biochemical properties including the increased exposure of CD4-induced epitopes (see Example 2) and the ability to bind to CXCR4 in the absence of CD4. Future studies of HIV-1/IIIBx and additional CD4-independent isolates should provide powerful tools to probe the structure and function of the viral envelope glycoprotein and lead to the rational design of gp120 molecules with altered immunogenic properties as therapeutic modalities.

EXAMPLE 2

Stable Exposure of the Coreceptor Binding Site in a CD4-independent HIV-1 Envelope Protein The experiments presented in this example may be summarized as follows.

The data presented previously in Example 1, disclose a CD4-independent HIV-1 virus, HIV-1/IIIBx, that interacts directly with the chemokine receptor CXCR4 to infect cells in the absence of CD4. The data presented herein disclose the underlying mechanism of the CD4-independence by using a novel cloned Env from the HIV-1/IIIBx swarm named 8x previously disclosed in Example 1. The 8x Env clone was used to produce soluble gp120. The data disclosed herein demonstrate that 8x gp120 bound directly to cells expressing only CXCR4 while binding of IIIB gp120 also required soluble CD4. Further, using an optical biosensor, the data disclosed herein demonstrate that CD4-induced (CD4i) epitopes recognized by monoclonal antibodies (MAbs) 17b and 48d were more exposed on 8x than on IIIB gp120. The ability of 8x gp120 to bind directly to CXCR4 land to react with MAbs 17b and 48d in the absence of CD4 indicates that 8x gp120 exists in a partially triggered but stable state in which the conserved coreceptor binding site in gp120, which overlaps with the 17b epitope, is exposed.

Substitution of the CXCR4-specific V3-loop of 8x with the V3-loop from the CCR5 tropic HIV-1/BaL strain resulted in an Env clone that mediated CD4-independent, CCR5-dependent virus infection. Therefore, the substitution of the V3-loop produced a gp120 chimera (8x-BaL) that bound to CCR5 in the absence of CD4. Thus, the data disclosed herein demonstrate that in a partially triggered Env protein, the V3-loop can alter the specificity of coreceptor use, but does not alter CD4 independence. Moreover, the data disclosed herein indicate that CD4 independence and chemokine coreceptor binding are dissociable. Further, HIV-1/IIIBx was far more sensitive to neutralization by HIV-positive human sera, a variety of anti-IIIB gp120 rabbit antisera, and CD4i MAbs than was the CD4-dependent IIIB strain. The increased sensitivity of HIV-1/IIIBx virus to neutralization by antibodies and the stable exposure of a highly conserved region of gp120suggest novel strategies for the development of antibodies and small molecule inhibitors to this functionally important domain.

The Materials and Methods used in the experiments presented in this Example are now described.

Plasmids

Human CCR5, CXCR4, and CD4 were expressed using the pCDNA3 vector (Invitrogen, San Diego, Calif.). The luciferase gene was expressed under control of the T7 promoter in the pGEM2 vector (Promega Corp., Madison, Wis.). The Envs from the HXBc2 clone of IIIB and 8x were both expressed in the pSP73 vector (Promega Corp., Madison, Wis.). To generate Env constructs containing the V3 loop of the R5 HIV-1 strain BaL, the KpnI-BamHI fragment in env from the full-length proviral clone pIIIB-V3BaL was cloned into pSP73-IIIB. To produce a version of 8x containing the V3 loop of BaL, the StuI-Bsu361 env fragment of pIIIB-V3BaL was cloned into pSP73-8x. Stop codons were inserted into each env plasmid at the gp120/gp41 junction using the Quickchange™ Site-Directed Mutagenesis Kit (Stratagene, La Jolla, Calif.) to make constructs for gp120 production. The identity of all mutants and clones was confirmed by DNA sequencing.

Cell-Cell Fusion Assay

This assay has been described in more detail elsewhere. Briefly, effector QT6 cells in T25 flasks were infected with recombinant vaccinia virus expressing T7 polymerase (vTF1.1) and transfected with 30 µg of env constructs wherein expression was driven by the T7 promoter. Target QT6 cells were plated in 24-well plates and each well of cells was transfected with 0.5 µg CD4 and 1.0 µg coreceptor plasmids under the control of the CMV promoter, and 1.5 µg of the luciferase reporter plasmid under the control of the T7 promoter. Following overnight expression, the effector cells were added to target cells and luciferase activity was quantified in cell lysates 7.5 hours after mixing.

Protein Production and Purification 293T cells were infected in T225 flasks with vTF1.1 and the cells were then transfected with 200 µg of gp120 plasmid. Four hours ppst-transfection, the cells were washed with phosphate buffered saline (PBS) and placed in serum-free media for 24 hours. Media was collected, clarified by centrifugation and 0.2 µM filtration prior to addition of 0.1% TX-100. Protein in the supernatant was bound to a *Galanthis Navalis* column (Vector Laboratories, Burlingame, Calif.), washed with methyl-α-D-mannopyranoside (MES) buffer (20 mM MES, pH 7.0, 0.13 M NaCl, 10 mM $CaCl_2$) and eluted in MES buffer containing 0.5M α-methyl mannoside. The eluate was subjected to additional purification, washing, and concentration using an Amicon ultrafiltration system with a 50 kD protein molecular weight cutoff. HPLC analysis determined that Env prepared in this fashion was highly pure, and accurate protein concentrations were determined by amino acid analysis and BCA assay.

Cell-Surface Binding Assay

Binding of gp120 to coreceptors was determined as described by Doranz et al. (1999, J. Virol., 73:2752–2761). Briefly, approximately 5 µg of each gp120 was iodinated using Iodogen (Pierce) to specific activities of 12.3 µCi/µg, 7.15 µCi/µg, 47.3 µCi/µg, and 22.0 µCi/µg for IIIB, 8x, IIIB-V3BaL, and 8x-V3BaL, respectively. One-hundred thousand counts per minute (CPM) was added to about 0.5 to about $1.0 \times 10^6$ 293T cells which had been transfected the previous day with 14 µg DNA in a total volume of 100 µl binding buffer (50 mM Hepes pH 7.4, 5 mM $MgCl_2$, 1 mM $CaCl_2$, 5% BSA). Soluble CD4 (sCD4) was added at 100 nM when indicated. The cells were incubated for 1 hour at 25° C.

Unbound radioactivity was removed by filtering the cells through Whatman GF/C filters presoaked in 0.3% polyethylenimine, and washing twice with 4 ml wash buffer (50 mM Hepes pH 7.4, 5 mM $MgCl_2$, 1 mM $CaCl_2$, 500 mM NaCl). The amount of radioactivity which bound nonspecifically to the filters in the absence of cells was subtracted from all data points.

Biosensor Experiments

All experiments were performed using a BIACORE 2000 (Upsala, Sweden) optical biosensor at 25° C. Approximately 200 RU of sCD4 and the full length human MAbs 17b and 48d were attached by amine coupling to a research grade CM5 chip. A naked sensor surface without antibody or sCD4 served as a negative control for each binding interaction. Env which had been serially diluted was run across each sensor surface at 6 different concentrations in a running buffer of PBS+0.005% Tween-20 (11 nM to 585 nM for gp120, 5 mM to 91 nM for gp120+sCD4). Soluble CD4 was added at an 8-fold molar excess to Env at least 30 minutes prior to measuring binding, and completely eliminated binding of Env to CD4 attached to the sensor surface. Binding and dissociation were measured for 300 seconds each at a flow rate of 30 µl/minute which gave a flow-independent binding on-rate. The sensor surface was regenerated between each binding reaction by using 2 washes of 10 mM HCl for 15 seconds at 100 µl/minute, which was found to return the signal completely to baseline without decreasing the binding capacity of the immobilized surface. Each binding curve was corrected for nonspecific binding by subtraction of the signal obtained from the negative control flow cell. Kinetic constants for association and dissociation were derived from linear transformations of the exported binding data of at least 5 concentrations of analyte. The kinetic parameters obtained were compared to those estimated by fitting the data to the simple 1:1 Langmuir interaction model using the BIA Evaluation 3.1 software.

Neutralization Assays

Neutralization of virus by antisera or MAbs was performed using a modification of the previously described MAGI assay (Chakerian et al., 1997, J. Virol. 71:3932–3939) or luciferase reporter virus system described by Connor et al. (1995, Virology 206:935–944). Briefly, $1.25 \times 10^5$ MAGI cells were plated in a 48-well plate, and the cells were allowed to adhere. The cells were infected with virus that had been pre-incubated with serial dilutions of antibody for 1 hour at 37° C. The amount of virus used was the amount previously determined with the MAGI assay to contain 400–800 infectious units. Twenty-four hours after infection, the DP178 inhibitory peptide was added at a final concentration of 5 µg/ml to prevent the formation of syncytia. The cell cultures were incubated another 48 hours, fixed and the cells were stained with X-gal. Blue nuclei were quantified using an AlphaImager 2000 (Alphalnnotech Corporation, San Leandro, Calif.). For luciferase reporter virus infections, equal amounts of virus, as judged by relative light units (RLU), were also incubated with serial dilutions of antibody for 1 hour at 37° C. Virus was added to GHOST-CCR5 cells in 96-well plates and cell lysates were measured for luciferase activity 2 days post-infection.

The Results of the experiments presented in this example are now described.

Direct Binding of 8x gp120 to CXCR4

Binding of CD4 to HIV-1 Env induces conformational changes required for subsequent Env-coreceptor interactions. These changes are likely to include increased exposure of an exceptionally well-conserved domain in gp120 that has been implicated in coreceptor binding (FIG. 12). Many SIV and HIV-2 strains can short-circuit this normal entry process by utilizing coreceptors for virus entry in a CD4-independent manner, although their efficiency is typically enhanced when CD4 is present. The data presented previously in Example 1 disclose production of a CD4-independent HIV-1 strain through repeated passaging of HIV-1 IIIB on CD4-negative, CXCR4-positive cells (Example 1, supra). The resulting virus strain (HIV-1/IIIBx) can utilize CXCR4 in the absence of CD4 to infect a wide variety of cell types (Example 1, supra). An Env clone derived from cells chronically infected with HIV-1/IIIBx, termed 8x, maintains this phenotype. Thus, cells expressing 8x Env mediated fusion with CD4-negative, CXCR4-positive cells. In the presence of CD4, fusion efficiency was enhanced approximately 3-fold (FIGS. 10A and 10B). Fusion mediated by 8x is strictly dependent upon CXCR4, and is not observed when other coreceptors are expressed (FIGS. 10A and 10B). Since CD4 is known to induce conformational changes in Env that enable it to interact with coreceptors and since the 8x Env can mediate CXCR4-dependent fusion in the absence of CD4, experiments were performed to determine whether the 8x Env protein exists in a partially triggered state, thereby enabling it to bind CXCR4 in a CD4-independent manner.

To evaluate conformational differences in the 8x gp120, the ability of purified 8x gp120 to bind directly to CXCR4 was examined. In this regard, a cell surface binding assay as described by Doranz et al. (1999, J. Virol., 73:2752–2761), and set forth herein, was used in which radioiodinated gp120, with or without prior incubation with soluble CD4 (sCD4), was added to cells expressing the desired coreceptor. The cells were washed and the amount of bound radiolabeled gp120 was measured. The data disclosed herein demonstrate that IIIB gp120 complexed with sCD4 bound to cells expressing CXCR4 but not to cells expressing other coreceptors (FIG. 11). In contrast, the 8x gp120 bound to CXCR4-expressing cells equally well in the presence or absence of sCD4 (FIG. 11). Binding to cells expressing vector alone or CCR5 was not observed. These results demonstrate that unlike the parental IIIB Env, the 8x gp120 exists in a stable conformation that enables it to interact directly with CXCR4 in the absence of CD4.

Exposure of the Coreceptor Binding Site

Without wishing to be bound by theory, the ability of 8x gp120 to bind to CXCR4 may be the result of increased exposure of sites on gp120 that interact with CXCR4. To determine whether there was increased exposure of these sites, the abilities of IIIB and 8x gp120 to interact with the CD4i MAbs 17b and 48d were examined. A Fab fragment of 17b was co-crystallized with gp120 and sCD4 (Kwong et al., 1998, Nature 393:648–659), and the data disclosed demonstrate that many of the contact residues involved in 17b-gp120 interactions are also important for coreceptor binding (FIG. 12). Thus, 17b can be used as an immunological surrogate to measure exposure of the conserved, coreceptor binding site defined by Rizzuto et al. (1998, Science 280:1949–1953).

Binding of IIIB and 8x gp120, with or without prior incubation with sCD4, to the CD4i MAbs 17b and 48d was measured using an optical biosensor assay method as described elsewhere herein (see materials and methods, Example 2). This approach makes it possible to measure protein-protein interactions in real time, and can be used to derive on- and off-rates as well as affinity constants. The desired MAb was covalently coupled to the sensor surface after which gp120 or gp120-sCD4 complexes were applied. A typical sensorgram is shown in FIG. 13. As expected, the rate at which HIV-1/IIIB gp120 bound to MAb 17b was markedly increased by prior incubation of Env with sCD4. Once bound to 17b, both IIIB gp120 and gp120-sCD4 complexes exhibited negligible off-rates. In contrast to IIIB gp120, 8x gp120 bound efficiently to 17b without sCD4, exhibiting an on-rate that was an order of magnitude greater than that of IIIB gp120. Addition of sCD4 enhanced this on-rate 2-fold. When complexed with sCD4, both the 8x and IIIB gp120s exhibited identical on-rates (Table 1). Interestingly, once bound to 17b, the 8x gp120 exhibited a greater off-rate than did IIIB gp120. This effect may be due to the Ile to Val mutation in the 8x gp120 at amino acid position 423 (FIG. 12), a residue previously shown to be a contact site for 17b (Kwong et al., supra).

TABLE 1

| | ka (l/Ms) | kd (l/s) | Kd (nM) |
|---|---|---|---|
| Binding to 17b | | | |
| 8x | $1 \times 10^5$ | $2 \times 10^{-3}$ | 15 |
| 8x/CD4 | $2 \times 10^5$ | $9 \times 10^{-4}$ | 4.5 |
| HXB | $8 \times 10^3$ | $2 \times 10^{-5}$ | 2.5 |
| HXB/CD4 | $3 \times 10^5$ | $5 \times 10^{-5}$ | 0.2 |
| Binding to 48d | | | |
| 8x | $2 \times 10^5$ | $1 \times 10^{-3}$ | 6.0 |
| 8x/CD4 | $3 \times 10^5$ | $6 \times 10^{-4}$ | 2.0 |

TABLE 1-continued

| | ka (1/Ms) | kd (1/s) | Kd (nM) |
|---|---|---|---|
| HXB | $1 \times 10^4$ | $5 \times 10^{-5}$ | 5.0 |
| HXB/CD4 | $5 \times 10^5$ | $3 \times 10^{-5}$ | 0.1 |

The data disclosed in Table 1 demonstrate the apparent kinetic and equilibrium constants derived from binding of gp120 to CD4i antibodies in biosensor experiments performed as described previously elsewhere herein. Briefly, the CD4i antibodies 17b and 48d were attached to the biosensor surface, and both binding and dissociation of serial dilutions of 8x and HXB gp120 were measured. Binding of serial dilutions of both Envs which had been premixed with a saturating amount of sCD4 was also determined. All bindings were performed at 25° C., and a sample sensorgram is shown in FIG. 13. The best fitted values for the slopes of the linearized plots of the data ($r^2 \geq 0.98$) are reported. The parameters estimated by fitting the simple 1:1 Langmuir interaction model globally were within 15% of the reported values. Values in italics represent dissociation rates that were so slow that they were at the limits of detection of the biosensor, making the affinity constants derived from these values less accurate.

Analysis of a different CD4i MAb, 48d, yielded results that were similar to 17b (Table 1). Finally, IIIB and 8x gp120 molecules interacted with CD4 attached to the sensor surface in an identical fashion. Thus, the mutations in 8x that render it CD4-independent did not affect CD4 binding to an appreciable degree, but did result in greater exposure of the 17b epitope, which overlaps with the conserved coreceptor binding site.

Dissociation of Coreceptor Choice and CD4-independence

Both the conserved coreceptor binding site as well as the V1/V2 and V3 loops of gp120 play important roles in Env-coreceptor interactions. Available evidence indicates that the V3 loop and, to a lesser extent, the V1/V2 region govern the number and types of coreceptors used by a given Env (Hoffman et al., 1998, Proc. Natl. Acad. Sci. U.S.A. 95:11360–11365; Ross and Cullen, 1998, Proc. Natl. Acad. Sci. U.S.A. 95:7682–7686; Speck et al., 1997, J. Virol. 71:7136–7139; Cocchi et al., 1996, Nature Med. 2:1244–1247; Cho et al., 1998, J. Virol. 72:2509–2515; Choe et al., 1996, Cell 85:1135–1148). In contrast, mutations in the conserved coreceptor binding site can affect Env-coreceptor binding (Rizzuto et al., 1998, Science 280:1949–1953), but it is not clear if this region also plays a role in coreceptor specificity. The ability of 8x gp120 to interact directly with CXCR4 provided an opportunity to determine if coreceptor choice and changes in Env that expose the coreceptor binding site are dissociable. Previous studies demonstrated that the introduction of an R5 V3-loop (from HIV-1 BaL) into an HIV-1 IIIB background resulted in an Env protein (IIIB-BaL) that used CCR5, but not CXCR4, for virus infection (Ross and Cullen, 1998, Proc. Natl. Acad. Sci. U.S.A. 95:7682–7686; Ross et al., 1997, J. Virol. 72:1918–1924). The data disclosed previously herein in Example 1 demonstrate, using a cell-cell fusion assay, that substituting the V3 loop of the 8x Env with that from an R5 Env (BaL) produced a protein (8x-BaL) that was able to mediate fission with CCR5-positive, CD4-negative cells. To determine if 8x-BaL could also mediate CD4-independent virus infection, luciferase reporter viruses as described in Connor et al. (1995, Virology 206:935–944) were generated bearing either IIIB-V3BaL or 8x-V3BaL Env proteins. Virions bearing 8x-V3BaL Env mediated CD4-independent, CCR5-dependent virus infection (FIG. 10B). As was observed with 8x Env in fusion assays, the presence of CD4 increased the efficiency of virus entry. Neither IIIB-BaL or 8x-BaL used CXCR4 in the presence or absence of CD4. Also, IIIB-BaL and 8x-BaL gp120 molecules were produced, and data disclosed herein demonstrate that IIIB-BAL gp120 bound to CCR5 in a CD4-dependent manner, while 8x-BaL bound to CCR5 independently of CD4. Neither protein bound to CXCR4 under any conditions examined. Thus, changes in the V3-loop affected which coreceptor was used, but did not impact CD4-independence.

Neutralization of HIV-1/IIIBx

Antibodies that block Env-coreceptor interactions can neutralize HIV-1 (Wu et al., 1996, Nature 384:179–183; Trkola et al., 1996, Nature 384:184–187). The exposed nature of the coreceptor binding site in HIV-1/IIIBx gp120 might therefore be expected to make this virus more sensitive to antibody mediated neutralization. Several SIV and HIV-1 strains with modifications in the V1/V2 region have been shown to be neutralization sensitive, presumably because of increased exposure of conserved determinants (Stamatatos and Cheng-Mayer, 1998, J. Virol. 72:7840–7845; Reitter et al., 1998, Nature Med. 4:679–684). Therefore, the relative sensitivities of HIV-1/IIIB and HIV-1/IIIBx to neutralization by HIV-positive human sera, and to sera from rabbits immunized with either IIIB or 8x gp120, were compared and the results are set forth in Table 2.

TABLE 2

| | | HIV-1 IIIB | | HIV-1 IIIBx | |
|---|---|---|---|---|---|
| Rabbit | Immunogen | 50% | 90% | 50% | 90% |
| 1169 | IIIB | 1,934 | 132 | 3,081 | 287 |
| 1170 | IIIB | 1,896 | 109 | 93,756 | 5,616 |
| 1171 | 8x | >10,240 | 1,005 | >163,840 | 13,748 |
| 1172 | 8x | 1,552 | 94 | 64,295 | 4,426 |
| Human sera ZT02575 | | 1,616 | 46 | 20,894 | 4,195 |
| Human sera JT2140 | | 155 | 11 | 892 | 187 |

| | IIIB- BaL | | 8x- BaL | |
|---|---|---|---|---|
| MAb 17b | 14 ng/ml | 90 ng/ml | 2 ng/ml | 15 ng/ml |
| MAb 48d | >5,000 ng/ml | >5,000 ng/ml | 3 ng/ml | >200 ng/ml* |
| MAb 50.1 | 95 ng/ml | 375 ng/ml | 45 ng/ml | 610 ng/ml |

The data disclosed in Table 2 were obtained by infecting sMAGI cells with equivalent amounts of HIV-1/IIIB and HIV-1/IIIBx. Infection was determined 72 hours after infection as previously described by Chackerian et al. (1997, J. Virol. 71:3932–3939). For MAbs 17b and 48d, equivalent amounts of luciferase reporter viruses bearing the IIIB-BAL or 8x-Bal Envs were used to infect GHOST-CCR5 cells which were lysed 48 hours post-infection. For all infections, virus and serial dilutions of MAbs, human sera, and rabbit sera were mixed for 1 hour prior to addition to the target cells. The concentration of sera or antibody required to neutralize 50% and 90% of input virus is indicated. MAb 48d did not neutralize IIIB-BAL under any condition tested, and only 88% neutralization of 8x-BaL was achieved by this MAb at a concentration of 200 ng/ml (as indicated by an *). MAb 50.1 is directed against BaL V3-loop as described by White-Scharf et al. (1993, Virology 192:197–206).

The data disclosed herein demonstrate that HIV-1/IIIBx was uniformly more sensitive to neutralization than the parental HIV-1/IIIB, in many cases by one-log or more (Table 2). HIV-1-positive human sera, rabbit sera generated against IIIB gp120, and rabbit sera generated against 8x gp120 all neutralized HIV-1/IIIBx far more efficiently than HIV-1/IIIB. In addition, the data disclosed herein demonstrate that virions containing 8x-BaL Env were much more sensitive to neutralization by the CD4i MAbs 17b and 48d than those containing IIIB-BaL Env, but 8x-BaL Env virions did not demonstrate increased sensitivity to neutralization by an antibody recognizing the V3 loop of these viruses (Table 2). Thus, without wishing to be bound by theory, the data disclosed herein demonstrate that increased exposure of the coreceptor binding site, as well as increased exposure of CD4i epitopes, is likely to account for the increased sensitivity of HIV-1/IIIBx to antibody-induced neutralization.

The prior art teaches that receptor binding triggers conformational changes in Env that activate its membrane fusion potential. Binding to CD4 enables Env to interact with an appropriate coreceptor (Wu et al., 1996, Nature 384:179–183; Trkola et al., 1996, Nature 384:184–187; Lapham et al., 1996, Science 274:602–605; Hill et al., 1997, J. Virol. 71:6296–6304), generally CCR5 or CXCR4, which is thought to result in additional conformational changes in Env that ultimately lead to membrane fusion and virus entry. Fusion is a critical step in virus infection, and understanding the structural intermediates in Env that lead to this process may suggest the development of novel anti-viral strategies. Indeed, early clinical trials with a peptide inhibitor of the membrane fusion reaction have shown significant reductions in viral load (Kilby et al., 1998, Nature Med. 4:1302–1307).

The discovery of the viral coreceptors and the recently solved crystal structure of a gp120 core fragment have provided greater understanding of the viral entry process and have identified new potential targets for pharmacologic or immunologic intervention (Kwong et al., 1998, Nature 393:648–659; Rizzuto et al., 1998, Science 280:1949–1953; Wyatt et al., 1998, Nature 393:705–710). In the case of Env, an exceptionally well conserved region in gp120 has been implicated in CCR5 binding (Rizzuto et al., 1998, Science 280:1949–1953). This region, located in the bridging sheet between the inner and outer domains of gp120, lies between the base of the V3 loop and the V1/V2 region (FIG. 12). Binding to CD4, which is known to reposition these variable regions (Wyatt et al., 1995, J. Virol. 69:5723–5733), may lead to exposure and/or formation of this highly conserved site. Neutralizing antibodies such as 17b bind to epitopes that overlap with this region (Rizzuto et al., 1998, Science 280:1949–1953; Wyatt et al., 1998, Nature 393:705–710), thus serving as immunological surrogates for exposure of this domain and suggesting that, if properly presented, this region may elicit broadly cross-reactive neutralizing antibodies. However, prior to the present invention, there was no way to present this region to the immune system in such a way to generate an immune response to the coreceptor binding region of gp120.

A number of HIV-1, HIV-2, and SIV virus strains have been described that bypass the normal viral entry process by interacting directly with CCR5 or CXCR4 to infect cells (Example 1; Edinger et al., 1997, Proc. Natl. Acad. Sci. U.S.A. 94:14742–14747; Endres et al., 1996, Cell 87:745–756). While CD4-independent viruses may impact viral tropism and pathogenesis, they also serve as useful tools for dissecting the virus entry pathway. The data disclosed herein demonstrate two lines of evidence indicating that the CD4-independent HIV-1 Env disclosed herein exists in a stable, partially triggered state in which the conserved coreceptor binding site is well exposed. First, 8x gp120 bound directly to CXCR4 while the parental IIIB gp120 bound CXCR4 in a CD4-dependent manner. Second, 8x gp120 bound much more rapidly to two CD4i MAbs than did the parental CD4-dependent protein. However, as a consequence of a faster off-rate, the overall affinity of 8x gp120 for CD4i MAbs was similar to that of HIV-1 IIIB gp120, providing a striking example of how important differences in protein-protein interactions can be revealed by the real time analysis afforded by the use of an optical biosensor. The faster off-rate exhibited by 8x relative to IIIB could be due to a number of amino acid changes in the 8x protein in the vicinity of the coreceptor binding site, including I423V, a residue which serves as a contact site for 17b (Kwong et al., 1998, Nature 393:648–659).

HIV-1 tropism is governed in large part by coreceptor choice. The ability of a virus to utilize CCR5, CXCR4, or both, largely dictates the type of CD4-positive cells it can enter. The V3 loop in gp120 plays a critical role in coreceptor choice, with the V1/2 region playing a more subsidiary role (Hoffman et al., 1998, Proc. Natl. Acad. Sci. U.S.A. 95:11360–11365; Ross and Cullen, 1998, Proc. Natl. Acad. Sci. U.S.A. 95:7682–7686; Speck et al., 1997, J. Virol. 71:7136–7139; Cocchi et al., 1996, Nature Med. 2:1244–1247; Cho et al., 1998, J. Virol. 72:2509–2515; Choe et al., 1996, Cell 85:1135–1148). The data disclosed herein demonstrate that the determinants underlying coreceptor choice and CD4-independence in 8x Env are dissociable. Thus, 8x Env containing a V3-loop from an R5 Env maintains its CD4-independent phenotype but now uses CCR5 rather than CXCR4 for cell-cell fusion and virus infection. Further, the data disclosed herein demonstrate that 8x-BaL gp120 is able to bind to CCR5-expressing cells in the absence of CD4. These data clearly demonstrate, for the first time, that coreceptor choice and CD4-independent use of a chemokine receptor are dissociable. These data suggest, without wishing to be bound by theory, that the coreceptor binding region can interact with both CXCR4 and CCR5, depending on the nature of the associated V3-loop (Rizzuto et al., 1998, Science 280:1949–1953). Thus, in the context of the HIV-1 variant disclosed herein, the V3-loop can affect coreceptor choice in a partially triggered Env as well. The disclosure of the present invention will facilitate the clarification of the respective roles the variable regions and the conserved binding site play in coreceptor interactions and the identification of the domains in CCR5 and CXCR4 with which each interacts.

A particularly striking feature of the HIV-1/IIIBx swarm and the 8x molecular clone was their sensitivity to neutralization by antibodies. HIV-1/IIIBx was approximately 10-fold more sensitive to neutralization by HIV-positive human sera as well as to rabbit sera generated against either IIIB gp120 or 8x gp120. Without wishing to be bound by theory, the increased sensitivity of HIV-1/IIIBx to antibody mediated neutralization suggests that one or more neutralization determinants in this partially triggered Env is more generally accessible to antibodies than in the parental, CD4-dependent Env. The conserved coreceptor binding site is a likely target that may account for this phenotype, as indicated by the ability of CD4i MAbs to bind directly to 8x Env and to efficiently neutralize 8x-BaL Env-pseudotyped virions. In addition, as demonstrated by the data disclosed in Example 1 herein, the 8x Env also exhibits a remarkable loss of 5 glycosylation sites relative to parental IIIB raising the possibility that the loss of carbohydrates could play a role in exposing this region. Despite the increased neutralization of 8x-BaL by CD4i MAbs, increased exposure of the coreceptor binding site did not lead to increased sensitivity of 8x-BaL to a MAb directed against the V3-loop (Table 2). Several other neutralization sensitive viruses have been described recently, including a SIVmac239 lacking glycosylation sites in the V1/V2 region, as well as a HIV-1 SF162 strain containing a deletion in V1 (Stamatatos and Cheng-Mayer, 1998, J. Virol. 72:7840–7845). The present invention will facilitate studies to determine whether the coreceptor binding site which adjoins the V1/V2 stem is exposed in these viruses as well.

Numerous studies have shown that immunization with recombinant gp120 typically fails to generate broadly cross-reactive neutralizing antibodies, yet it is clear that such antibodies are generated in some individuals as a consequence of virus infection (Burton and Motefiori, 1997, AIDS 11 (Supp. A):S87–S98). Without wishing to be bound by theory, it may be that only strain-specific neutralization has been observed following immunization by gp120 because conserved regions of Env are sequestered in CD4-dependent gp120s prior to CD4 binding. The data disclosed herein suggest that if CD4-independence results from the partially triggered form of gp120 which no longer requires the initial binding to CD4 before the protein will bind to the chemokine receptor protein, then exposure of the highly conserved chemokine receptor binding site renders the virus more sensitive to neutralization. More importantly, the data disclosed herein suggest indicate that immunization with Envs that are partially triggered thus stably exposing the otherwise hidden chemokine receptor binding site may result in more efficient generation of broadly cross-reactive neutralizing antibodies directed against this region. For this to occur, antibodies must be generated that can access the coreceptor binding site in native, CD4-dependent Env proteins, perhaps after CD4-binding induces a triggered conformation in which access to this region is enhanced. Identifying determinants that render Envs CD4-independent and that influence exposure of this region will make it possible to systematically address the potential of this site to elicit neutralizing antibodies. It is important to note that while exposure of the coreceptor binding site may be an important component of CD4-independent Envs, other changes in Env are also likely to influence the ability to infect cells in a CD4-independent manner (Example 1).

In addition, the ability to examine and map, at the molecular level, the chemokine receptor binding site determinant(s) will facilitate the development of small-molecule inhibitors of gp120/chemokine receptor binding.

A "small-molecule," as the term is used herein, means a compound, whether synthetic or naturally occurring, including nucleic acids and polypeptides, such as, but not limited to, peptidomimetics and ALX40-4C (Doranz et al., 1997, J. Exp. med. 186:1395–1400), which are capable of inhibiting gp120 binding to a chemokine receptor protein, and which are less than about 1 kDa in size.

Therefore, the data disclosed herein have important implications in the development of effective antiviral therapeutics including, but not limited to, antibody-based modalities. Thus, the present invention should be construed to encompass the development of a wide class of compounds as inhibitors of gp120/chemokine receptor protein interactions.

Further, that the coreceptor binding site can be stably exposed may have implications for viral entry. Without wishing to be bound by theory, it is conceivable that exposure and/or formation of the coreceptor binding site subsequent to CD4 binding could result in a conformation of Env that is relatively unstable, requiring interactions with a coreceptor within a short period of time. For example, triggering the conformational change in the Semliki Forest virus spike glycoprotein by acid pH leads to rapid inactivation of the protein's membrane fusion potential unless it can interact with its lipid coreceptors within several minutes (Kielian, 1995, Advances in Virus Res. 45:113–151). However, the 8x Env protein, which exists in a partially triggered but stable state, suggests that exposure of the coreceptor binding site is compatible with a long-lived triggered Env conformation. Thus, coreceptor binding could occur long after the conformational changes induced by CD4 that make this event possible, perhaps accounting for the ability of HIV-1 to infect cells that express very low levels of coreceptor when adequate levels of CD4 are present (Platt et al., 1998, J.

Virol. 72:2855–2864; Kozak et al., 1997, J. Virol. 71:873–882). This discovery further emphasizes the potential of the present invention in the development of antiviral therapeutics based on the inhibition of HIV-1/chemokine receptor interactions since the triggered conformation may potentially be present long enough for compounds blocking the necessary determinants to effect the inhibition of virus binding to the host cell receptors.

In conclusion, the data disclosed herein demonstrate that the CD4-independent phenotype of the 8x Env protein is associated with stable exposure of the coreceptor binding site. Thus, this protein likely represents a structural intermediate of the normal fusion process, and can be used to investigate the structural parameters that influence the conformational changes that lead to membrane fusion. Importantly, the highly conserved nature of this stably exposed domain and the fact the neutralizing antibodies can be directed against it raise the possibility that this domain, if properly presented, can be used to elicit broadly cross-reactive neutralizing antibodies against HIV-1.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a CD4-independent HIV env having the nucleotide sequence of SEQ ID NO:4.

2. A vector comprising the isolated nucleic acid of claim 1.

3. A cell comprising the isolated nucleic acid of claim 1.

* * * * *

SEQUENCE LISTING

<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 1
cgcaacctat accaatagta gcaa                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 2
cagtaagcca tccaatcaca ctac                                            24

<210> SEQ ID NO 3
<211> LENGTH: 726
<212> TYPE: PRT
<213> ORGANISM: Human immunodeficiency virus type 1

<400> SEQUENCE: 3

```
Met Arg Val Lys Glu Lys Tyr Gln His Leu Trp Arg Trp Gly Trp Arg
  1               5                  10                  15

Trp Gly Thr Met Leu Leu Gly Met Leu Met Ile Cys Asn Ala Thr Glu
                 20                  25                  30

Lys Leu Trp Val Thr Val Tyr Tyr Gly Val Pro Val Trp Lys Glu Ala
             35                  40                  45

Thr Thr Thr Leu Phe Cys Ala Ser Asp Ala Lys Ala Tyr Glu Thr Glu
         50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Gly Ser
    130                 135                 140

Gly Arg Met Ile Met Glu Lys Gly Glu Ile Lys Asn Cys Ser Phe Asn
145                 150                 155                 160

Ile Ser Thr Ser Lys Arg Ser Lys Val Lys Lys Glu Tyr Ala Phe Phe
                165                 170                 175

Tyr Lys Leu Asp Ile Ile Pro Ile Asp Asn Asp Pro Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
```

-continued

```
            225                 230                 235                 240
    Asn Val Ser Thr Val Gln Cys Thr His Gly Ile Arg Pro Val Val Ser
                        245                 250                 255
    Thr Gln Leu Leu Leu Asn Gly Ser Leu Ala Glu Glu Val Val Ile
                260                 265                 270
    Arg Ser Val Asn Phe Thr Asp Asn Ala Lys Thr Ile Ile Val Gln Leu
                275                 280                 285
    Asn Thr Ser Val Glu Ile Asn Cys Thr Lys Pro Asn Asn Thr Arg
            290                 295                 300
    Lys Arg Ile Arg Ile His Arg Gly Pro Gly Arg Ala Phe Val Thr Val
    305                 310                 315                 320
    Gly Lys Ile Gly Asn Met Arg Gln Ala His Cys Asn Ile Ser Arg Ala
                        325                 330                 335
    Lys Trp Ser Asn Thr Leu Lys Gln Ile Ala Ser Lys Leu Arg Glu Gln
                    340                 345                 350
    Phe Gly Asn Asn Lys Thr Ile Ile Phe Lys Gln Ser Ser Gly Gly Asp
                355                 360                 365
    Pro Glu Ile Val Thr His Ser Phe Asn Cys Gly Gly Glu Phe Phe Tyr
            370                 375                 380
    Cys Lys Ser Thr Gln Leu Phe Asn Ser Thr Trp Ser Thr Lys Gly Ser
    385                 390                 395                 400
    Asn Asn Thr Glu Gly Ser Asp Thr Ile Thr Leu Pro Cys Arg Ile Lys
                        405                 410                 415
    Gln Val Ile Asn Met Trp Gln Glu Val Gly Lys Ala Met Tyr Ala Pro
                    420                 425                 430
    Pro Ile Ser Gly Gln Ile Arg Cys Ser Ser Asn Ile Thr Gly Leu Leu
                435                 440                 445
    Leu Thr Arg Asp Gly Gly Asn Ser Asn Asn Glu Ser Glu Ile Phe Arg
            450                 455                 460
    Pro Gly Gly Gly Asp Met Arg Asp Asn Trp Arg Ser Glu Leu Tyr Lys
    465                 470                 475                 480
    Tyr Lys Val Val Lys Ile Glu Pro Leu Gly Val Ala Pro Thr Lys Ala
                        485                 490                 495
    Lys Arg Arg Val Val Gln Arg Glu Lys Arg Ala Val Gly Ile Gly Ala
                    500                 505                 510
    Leu Phe Leu Gly Phe Leu Gly Ala Ala Gly Ser Thr Met Gly Ala Ala
                515                 520                 525
    Ser Met Ala Leu Thr Val Gln Ala Arg Gln Ser Leu Ser Gly Ile Val
            530                 535                 540
    Gln Gln Gln Asn Asn Leu Leu Arg Ala Ile Glu Ala Gln Gln His Leu
    545                 550                 555                 560
    Leu Gln Leu Thr Val Trp Gly Ile Lys Gln Leu Gln Ala Arg Ile Leu
                        565                 570                 575
    Ala Val Glu Arg Tyr Leu Lys Asp Gln Gln Leu Leu Gly Ile Trp Gly
                    580                 585                 590
    Cys Ser Gly Lys Leu Ile Cys Thr Thr Ala Val Pro Trp Asn Ala Ser
                595                 600                 605
    Trp Ser Asn Lys Ser Leu Glu Gln Ile Trp Asn Asn Met Thr Trp Met
            610                 615                 620
    Glu Trp Asp Arg Glu Ile Asn Asn Tyr Thr Ser Leu Ile His Ser Leu
    625                 630                 635                 640
    Ile Glu Glu Ser Gln Ile Gln Gln Glu Met Asn Glu Gln Glu Leu Leu
                        645                 650                 655
```

```
Glu Leu Asp Lys Trp Ala Ser Leu Trp Asn Trp Phe Asn Ile Thr Asn
            660                 665                 670
Trp Leu Trp Tyr Ile Lys Leu Phe Ile Met Ile Val Gly Gly Leu Val
        675                 680                 685
Gly Leu Arg Ile Val Phe Ala Val Leu Ser Val Val Lys Lys Leu Gly
    690                 695                 700
Arg Asp Ile His His Tyr Arg Phe Arg Pro Thr Ser Gln His Arg Gly
705                 710                 715                 720
Asp Thr Gly Pro Lys Glu
            725

<210> SEQ ID NO 4
<211> LENGTH: 2184
<212> TYPE: DNA
<213> ORGANISM: Human immunodeficiency virus type 1

<400> SEQUENCE: 4
atgagagtga aggagaaata tcagcacttg tggagatggg ggtggagatg gggcaccatg      60
ctccttggga tgttgatgat ctgtaatgct acagaaaaat tgtgggtcac agtctattat     120
ggggtacctg tgtggaagga agcaaccacc actctatttt gtgcatcaga tgctaaagca     180
tatgaaacag aggtacataa tgtttgggcc acacatgcct gtgtacccac agaccccaac     240
ccacaagaag tagtattggt aaatgtgaca gaaaatttta acatgtggaa aaatgacatg     300
gtagaacaga tgcatgagga tataatcagt ttatgggatc aaagcctaaa gccatgtgta     360
aaattaaccc cactctgtgt tagtttaaag tgcactgatt tgaagaatga tactaatacc     420
aatagtggta gcgggagaat gataatggag aaggagagag taaaaaactg ctctttcaat     480
atcagcacaa gcaaaagaag taaggtgaag aaagaatatg catttttta taaacttgat     540
ataataccaa tagataatga tcctaccagc tatacgttga caagttgtaa cacctcagtc     600
attacacagg cctgtccaaa ggtatccttt gagccaattc ccatacatta ttgtgccccg     660
gctggttttg cgattctaaa atgtaataat aagacgttca atggaacagg accatgtaca     720
aatgtcagca cagtacaatg tacacatgga attaggccag tagtatcaac tcaactgctg     780
ttaaatggca gtctagcaga agaagaggta gtaattagat ctgtcaattt cacggacaat     840
gctaaaacca taatagtaca gctgaacaca tctgtagaaa ttaattgtac aaaacccaac     900
aacaatacaa gaaaagaat ccgtatccat agaggaccag ggagagcatt tgttacagta     960
ggaaaaatag gaaatatgag acaagcacat tgtaacatta gtagagcaaa atggagtaac    1020
actttaaaac agatagctag caaattaaga gaacaatttg gaaataataa aacaataatc    1080
tttaagcagt cctcaggagg ggacccagaa attgtaacgc acagttttaa ttgtggaggg    1140
gaatttttct actgtaagtc aacacaactg tttaatagta cttggagtac taaagggtca    1200
aataacactg aaggaagtga cacaatcacc ctcccatgca gaataaaaca agttataaac    1260
atgtggcagg aagtaggaaa agcaatgtat gcccctccca tcagtggaca aattagatgt    1320
tcatcaaata ttacagggct gctattaaca agagatggtg gtaatagcaa caatgagtcc    1380
gagatcttca gacctggagg aggagatatg agggacaatt ggagaagtga attatataaa    1440
tataaagtag taaaaattga accattagga gtagcaccca ccaaggcaaa gagaagagtg    1500
gtgcagagag aaaaaagagc agtgggaata ggagctttgt tccttgggtt cttgggagca    1560
gcaggaagca ctatgggcgc agcgtcaatg gcgctgacgg tacaggccag acaatcattg    1620
tctggtatag tgcagcagca gaacaatctg ctgagggcta ttgaggcgca acagcatctg    1680
```

```
ttgcaactca cagtctgggg catcaagcag ctccaggcaa gaatcctggc tgtggaaaga    1740
tacctaaagg atcaacagct cctggggatt tggggttgct ctggaaaact catttgcacc    1800
actgctgtgc cttggaatgc tagttggagt aataaatctc tggaacagat ttggaataac    1860
atgacctgga tggagtggga cagagaaatt aacaattaca caagcttaat acactcctta    1920
attgaagaat cgcaaatcca gcaagaaatg aatgaacaag aattattgga attagataaa    1980
tgggcaagtt tgtggaattg gtttaacata acaaattggc tgtggtatat aaaattattc    2040
ataatgatag taggaggctt ggtaggttta agaatagttt ttgctgtact ttctgtagtg    2100
aaaaagttag caggatat tcaccattat cgtttcagac ccacctccca acaccgaggg    2160
gacccgacag gcccgaagga atag                                          2184
```

```
<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 5
cctcaggagg ggacccagaa attgtaacgc                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 6
gcgttacaat ttctgggtcc cctcctgagg                                    30

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 7
ggcaggaagt agaaaaagca atgtatgccc c                                  31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 8
ggggcataca ttgcttttc tacttcctgc c                                   31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 9
ggcaggaagt aggaaaagca atgtatgccc c                                  31
```

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 10
ggggcataca ttgcttttcc tacttcctgc c                       31

<210> SEQ ID NO 11
<211> LENGTH: 856
<212> TYPE: PRT
<213> ORGANISM: Human immunodeficiency virus type 1

<400> SEQUENCE: 11

Met Arg Val Lys Glu Lys Tyr Gln His Leu Trp Arg Trp Gly Trp Arg
 1               5                  10                  15

Trp Gly Thr Met Leu Leu Gly Met Leu Met Ile Cys Asn Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asp Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Ser
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

-continued

```
Gly Lys Ile Gly Asn Met Arg Gln Ala His Cys Asn Ile Ser Arg Ala
            325                 330                 335
Lys Trp Asn Asn Thr Leu Lys Gln Ile Asp Ser Lys Leu Arg Glu Gln
            340                 345                 350
Phe Gly Asn Asn Lys Thr Ile Ile Phe Lys Gln Ser Ser Gly Gly Asp
            355                 360                 365
Pro Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
            405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
            435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
            485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
            515                 520                 525
Thr Met Gly Ala Ala Ser Met Thr Leu Thr Val Gln Ala Arg Gln Leu
            530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
            565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
            595                 600                 605
Pro Trp Asn Ala Ser Trp Ser Asn Lys Ser Leu Glu Gln Ile Trp Asn
            610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
            645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
            675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
            725                 730                 735
```

```
Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 12
<211> LENGTH: 759
<212> TYPE: PRT
<213> ORGANISM: Human immunodeficiency virus type 1

<400> SEQUENCE: 12

Met Arg Val Lys Glu Lys Tyr Gln His Leu Trp Arg Trp Gly Trp Arg
  1               5                  10                  15

Trp Gly Thr Met Leu Leu Gly Met Leu Met Ile Cys Asn Ala Thr Glu
             20                  25                  30

Lys Leu Trp Val Thr Val Tyr Tyr Gly Val Pro Val Trp Lys Glu Ala
         35                  40                  45

Thr Thr Thr Leu Phe Cys Ala Ser Asp Ala Lys Ala Tyr Glu Thr Glu
     50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Lys Arg Gly Lys Val Lys Lys Glu Tyr Ala Phe Phe
                165                 170                 175

Tyr Lys Leu Asp Ile Ile Pro Ile Asp Asn Asp Pro Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255
```

-continued

```
Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Lys Pro Asn Asn Asn Thr Arg
            290                 295                 300

Lys Arg Ile Arg Ile Gln Arg Gly Pro Gly Arg Ala Phe Val Thr Val
305                 310                 315                 320

Gly Lys Ile Gly Asn Met Arg Gln Ala His Cys Asn Ile Ser Arg Ala
                325                 330                 335

Lys Trp Ser Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
            370                 375                 380

Cys Lys Ser Thr Gln Leu Phe Asn Ser Thr Trp Ser Thr Lys Gly Ser
385                 390                 395                 400

Asn Asn Thr Glu Gly Ser Asp Thr Ile Thr Leu Pro Cys Arg Ile Lys
                405                 410                 415

Gln Ile Ile Asn Met Trp Gln Lys Val Glu Lys Ala Met Tyr Ala Pro
                420                 425                 430

Pro Ile Ser Gly Gln Ile Arg Cys Ser Ser Asn Ile Thr Gly Leu Leu
            435                 440                 445

Leu Thr Arg Asp Gly Gly Asn Asn Asn Glu Ser Glu Ile Phe Arg
            450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
                485                 490                 495

Lys Arg Arg Val Val Gln Arg Glu Lys Arg Ala Val Gly Ile Gly Ala
            500                 505                 510

Leu Phe Leu Gly Phe Leu Gly Ala Ala Gly Ser Thr Met Gly Ala Ala
            515                 520                 525

Ser Met Ala Leu Thr Val Gln Ala Arg Gln Ser Leu Ser Gly Ile Val
530                 535                 540

Gln Gln Gln Asn Asn Leu Leu Arg Ala Ile Glu Ala Gln Gln His Leu
545                 550                 555                 560

Leu Gln Leu Thr Val Trp Gly Ile Lys Gln Leu Gln Ala Arg Ile Leu
                565                 570                 575

Ala Val Glu Arg Tyr Leu Lys Asp Gln Gln Leu Leu Gly Ile Trp Gly
            580                 585                 590

Cys Ser Gly Lys Leu Ile Cys Thr Thr Ala Val Pro Trp Ser Ala Ser
            595                 600                 605

Trp Ser Asn Lys Ser Leu Glu Gln Ile Trp Asn Asn Met Thr Trp Met
            610                 615                 620

Glu Trp Asp Arg Glu Ile Asn Asn Tyr Thr Ser Leu Ile His Ser Leu
625                 630                 635                 640

Ile Glu Glu Ser Gln Asn Gln Gln Glu Met Asn Glu Gln Glu Leu Leu
                645                 650                 655

Glu Leu Asp Lys Trp Ala Ser Leu Trp Asn Trp Phe Ile Ile Ser Ser
            660                 665                 670
```

-continued

```
Trp Leu Trp Tyr Ile Lys Ile Phe Ile Met Ile Val Gly Gly Leu Val
        675                 680                 685

Gly Leu Arg Ile Val Phe Ala Val Phe Ser Ile Val Asn Arg Val Arg
    690                 695                 700

Gln Gly Tyr Ser Pro Leu Ser Phe Gln Thr His Leu Pro Ile Pro Lys
705                 710                 715                 720

Gly Pro Asp Arg Pro Lys Arg Ile Leu Asn Thr Tyr Leu Gly Arg Ser
                725                 730                 735

Ala Glu Pro Val Pro Leu Gln Leu Pro Pro Leu Glu Arg Leu Ser Gly
            740                 745                 750

Thr Leu Asp Cys Asn Lys Asp
        755
```